United States Patent
Brown, Jr. et al.

(10) Patent No.: US 11,740,235 B2
(45) Date of Patent: Aug. 29, 2023

(54) MODEL-MEMBRANE-BASED LIPID TRANSFER ASSAYS AND METHODS

(71) Applicant: Regents of the University of Minnesota, Minneapolis, MN (US)

(72) Inventors: Rhoderick Edmiston Brown, Jr., Austin, MN (US); Yong-guang Gao, Austin, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 382 days.

(21) Appl. No.: 16/998,634

(22) Filed: Aug. 20, 2020

(65) Prior Publication Data
US 2021/0055294 A1     Feb. 25, 2021

Related U.S. Application Data

(60) Provisional application No. 62/890,238, filed on Aug. 22, 2019.

(51) Int. Cl.
    *G01N 33/00*     (2006.01)
    *G01N 33/543*     (2006.01)
    *G01N 33/53*     (2006.01)
    *G01N 33/58*     (2006.01)
    *G01N 33/533*     (2006.01)

(52) U.S. Cl.
    CPC ..... *G01N 33/54393* (2013.01); *G01N 33/533* (2013.01); *G01N 33/5306* (2013.01); *G01N 33/5308* (2013.01); *G01N 33/54306* (2013.01); *G01N 33/582* (2013.01)

(58) Field of Classification Search
    CPC ................................................ G01N 33/54393
    USPC ........................................................... 436/71
    See application file for complete search history.

(56) References Cited

U.S. PATENT DOCUMENTS

| | | |
|---|---|---|
| 5,585,235 A | 12/1996 | Brocia |
| 6,297,059 B1 | 10/2001 | Song et al. |
| 8,318,449 B2 | 11/2012 | Fukuchi |
| 2009/0047700 A1 | 2/2009 | Hussain et al. |
| 2012/0016000 A1 | 1/2012 | Hussain et al. |

OTHER PUBLICATIONS

Kenoth, R., Brown, R.E., Kamlekar, R.K. (2019). In Vitro Measurement of Sphingolipid Intermembrane Transport Illustrated by GLTP Superfamily Members. In: Drin, G. (eds) Intracellular Lipid Transport. Methods in Molecular Biology, vol. 1949. Humana Press, New York, NY. (Year: 2019).*
Beaugrand et al., Lipid concentration and molar ratio boundaries for the use of isotropic bicelles. *Langmuir* 30, 6162-6170 (2014).

(Continued)

*Primary Examiner* — Christine T Mui
*Assistant Examiner* — Emily R. Berkeley
(74) *Attorney, Agent, or Firm* — Mueting Raasch Group

(57) ABSTRACT

An assay system for measuring transfer of lipid from a donor model biomembrane to an acceptor model biomembrane generally includes a donor model biomembrane that has a lipid with a detectable label, a lipid transfer protein that specifically binds the detectable lipid, and an acceptor model biomembrane. At least one of the donor model biomembrane and the acceptor model biomembrane is a bicelle-dilution model membrane.

10 Claims, 16 Drawing Sheets

(56) References Cited

OTHER PUBLICATIONS

Biverstahl et al., Biophysical studies of the membrane location of the voltage-gated sensors in the HsapBK and KvAP K(+) channels. *Biochim Biophys Acta* 1788, 1976-1986 (2009).

Boldyrev et al., An Expedient Synthesis of Fluorescent Labeled Ceramide-1-phosphate Analogues. *Russ J Bioorg Chem* 39, 539-542 (2013).

Boldyrev et al., New BODIPY lipid probes for fluorescence studies of membranes. *J Lipid Res* 48, 1518-1532 (2007).

Brown et al., Glycolipid transfer proteins. *Biochim Biophys Acta* 1771, 746-760 (2007).

Durr et al., The magic of bicelles lights up membrane protein structure. *Chem Rev* 112, 6054-6074 (2012).

Durr et al., When detergent meets bilayer: birth and coming of age of lipid bicelles. *Prog Nucl Magn Reson Spectrosc* 69, 1-22 (2013).

Gao et al., Measuring Lipid Transfer Protein Activity Using Bicelle-Dilution Model Membranes. *Anal Chem* 92, 3417-3425 (2020).

Glover et al., Structural evaluation of phospholipid bicelles for solution-state studies of membrane-associated biomolecules. *Biophys J* 2163-2171 (2001).

Hirano et al., Structural basis of phosphatidylcholine recognition by the C2-domain of cytosolic phospholipase $A_2$ α. *Elife* 8, e44760 (2019).

Lai et al., Kinetics of lipid mixing between bicelles and nanolipoprotein particles. *Biophys Chem* 197, 47-52 (2015).

Lai et al., Integral membrane protein fragment recombination after transfer from nanolipoprotein particles to bicelles. *Biochemistry* 52, 9405-9412 (2013).

Li et al., Human glycolipid transfer protein: probing conformation using fluorescence spectroscopy. *Biochemistry* 43, 10285-10294 (2004).

Liebau et al., Characterization of fast-tumbling isotropic bicelles by PFG diffusion NMR. *Magn Reson Chem* 55, 395-404 (2017).

Lin et al., Cloning and expression of glycolipid transfer protein from bovine and porcine brain, *J Biol Chem* 275, 5104-5110 (2000).

Malakhova et al., Point mutational analysis of the liganding site in human glycolipid transfer protein. Functionality of the complex. *J Biol Chem* 280, 26312-26320 (2005).

Mattjus et al., A fluorescence resonance energy transfer approach for monitoring protein-mediated glycolipid transfer between vesicle membranes. *Anal Biochem* 268, 297-304 (1999).

National Center for Biotechnology Information, National Library of Medicine, National Institutes of Health, GenBank Locus NP_181016, Accession No. NP_181016, "Glycolipid transfer protein (GLTP) family protein [*Arabidopsis thaliana*]," [online]. Bethesda, MD [retrieved on Mar. 17, 2021]. Retrieved from the Internet: <URL:https://www.ncbi.nlm.nih.gov/protein/NP_181016>; 2 pages.

National Center for Biotechnology Information, National Library of Medicine, National Institutes of Health, GenBank Locus NP_077792, Accession No. NP_077792, "Ceramide-1-phosphate transfer protein [Mus musculus]," [online]. Bethesda, MD [retrieved on Mar. 17, 2021]. Retrieved from the Internet: <URL:https://www.ncbi.nlm.nih.gov/protein/NP_077792.2>; 2 pages.

National Center for Biotechnology Information, National Library of Medicine, National Institutes of Health, GenBank Locus JN542538, Accession No. JN542538, "Homo sapiens ceramide-1-phosphate transfer protein (GLTPD1) mRNA, complete cds," [online]. Bethesda, MD [retrieved on Mar. 17, 2021]. Retrieved from the Internet: <URL:https://www.ncbi.nlm.nih.gov/nuccore/JN542538>; 1 page.

National Center for Biotechnology Information, National Library of Medicine, National Institutes of Health, GenBank Locus AF209704, Accession No. AF209704, "Homo sapiens glycolipid transfer protein mRNA, complete cds," [online]. Bethesda, MD [retrieved on Mar. 17, 2021]. Retrieved from the Internet: <URL:https://www.ncbi.nlm.nih.gov/nuccore/AF209704>; 2 pages.

Rowe et al., Fluorescence probe study of bicelle structure as a function of temperature: developing a practical bicelle structure model. *Langmuir* 19, 2039-2048 (2003).

Simanshu et al., Non-vesicular trafficking by a ceramide-1-phosphate transfer protein regulates eicosanoids. *Nature* 500, 463-467 (2013).

Simanshu et al., Arabidopsis accelerated cell death 11, ACD11, is a ceramide-1-phosphate transfer protein and intermediary regulator of phytoceramide levels. *Cell Rep* 6, 388-399 (2014).

Wu et al., Assessing the size, stability, and utility of isotropically tumbling bicelle systems for structural biology. *Biochim Biophys Acta* 1798, 482-488 (2010).

Zhai et al., Phosphatidylserine Stimulates Ceramide 1-Phosphate (C1P) Intermembrane Transfer by C1P Transfer Proteins. *J Biol Chem* 292, 2531-2541 (2017).

\* cited by examiner

FIG. 8
(A)
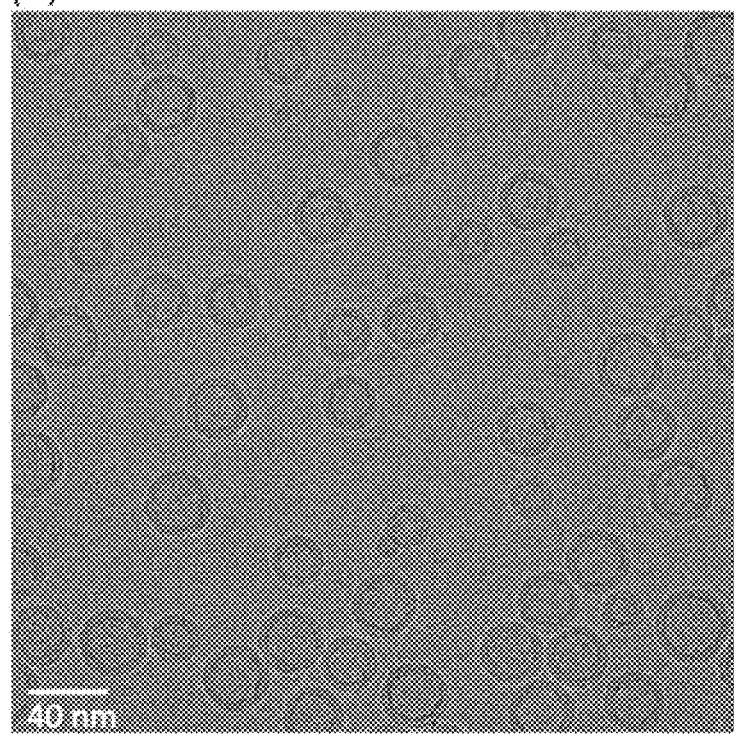
(B)
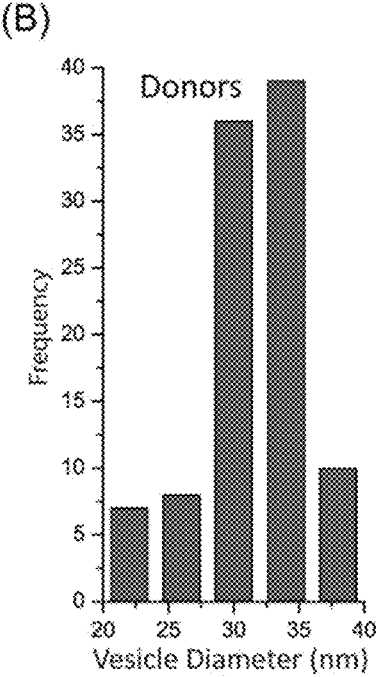

FIG. 9
(A)
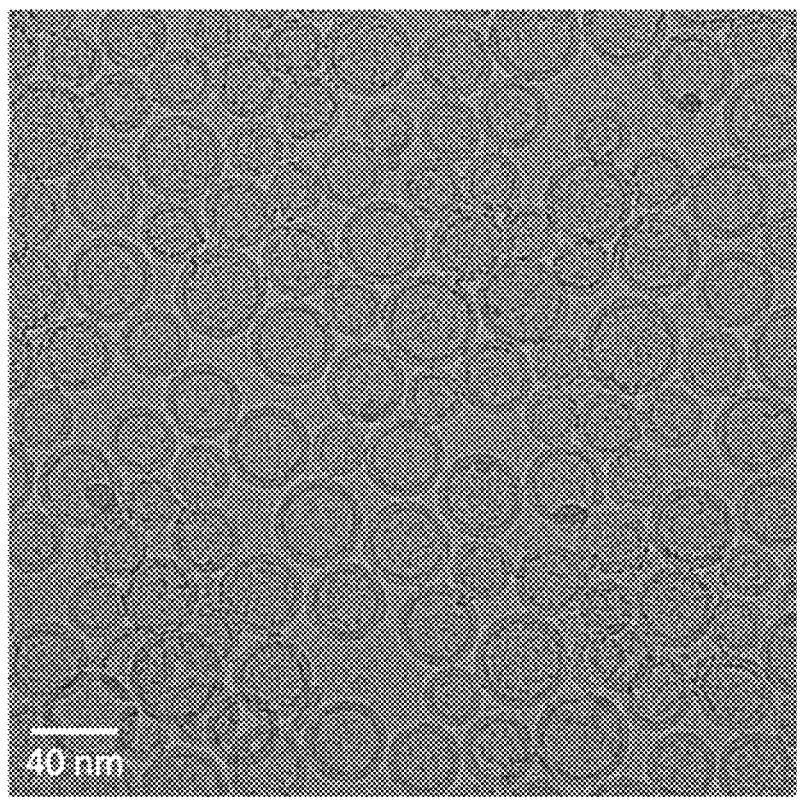
(B)
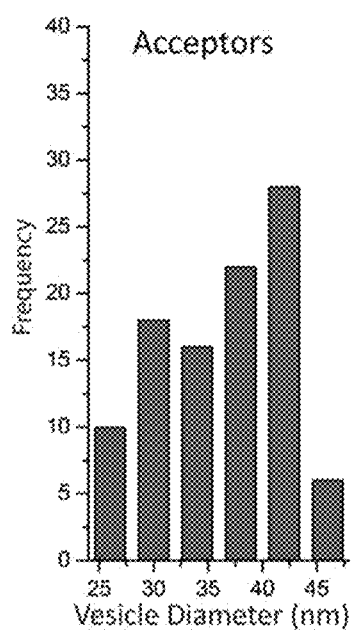

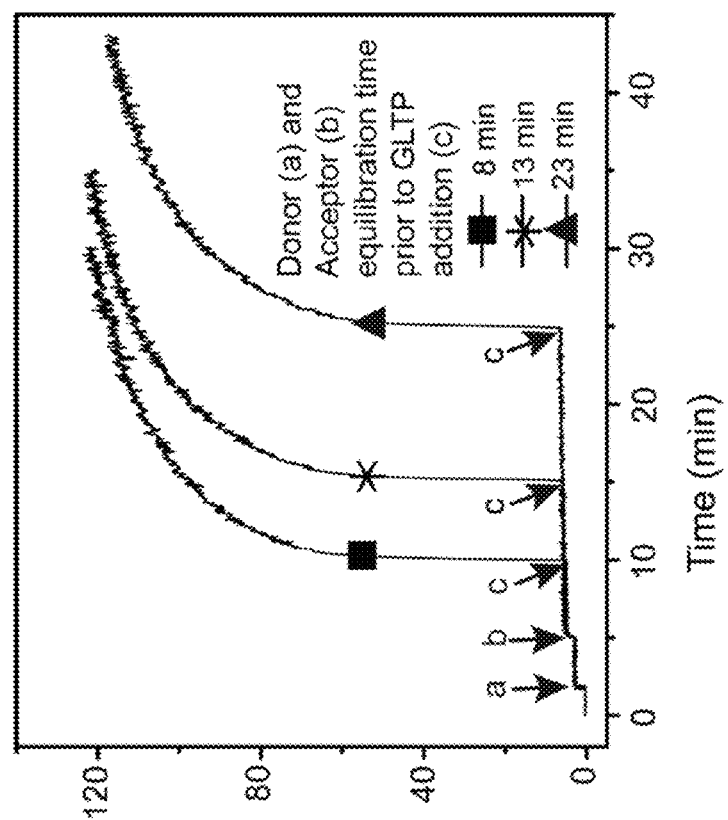
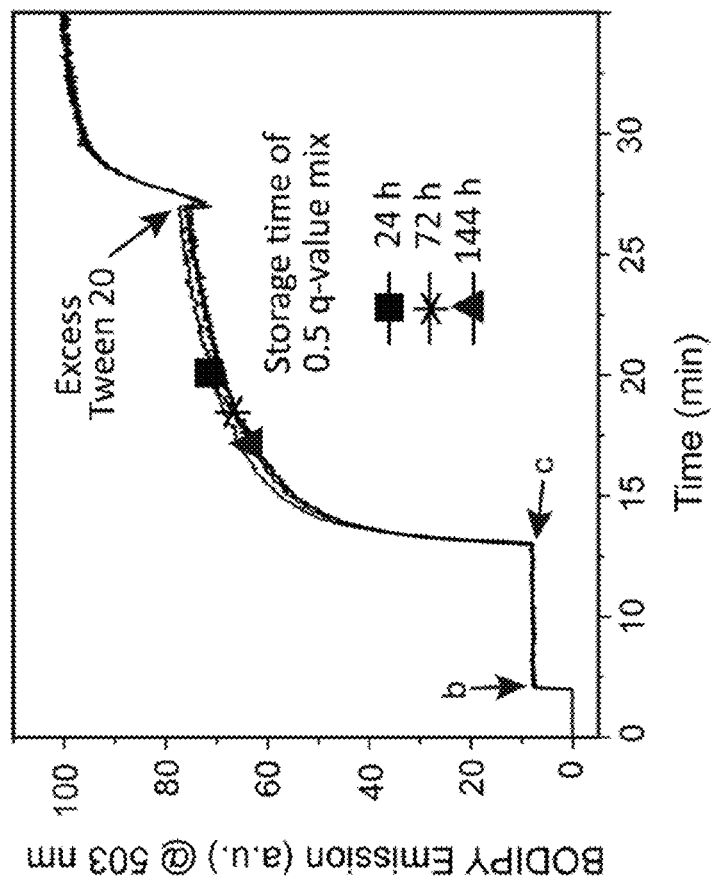
FIG. 10

FIG. 11
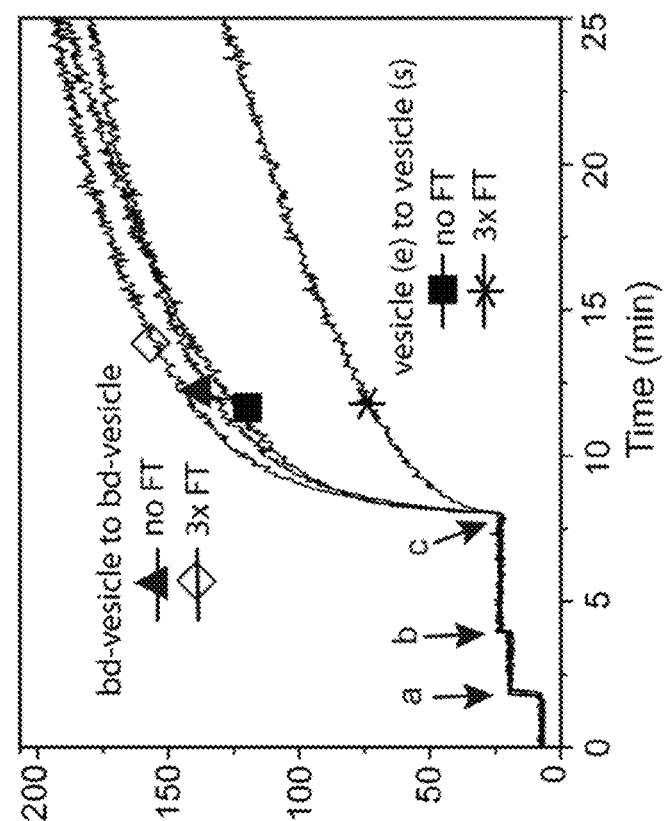
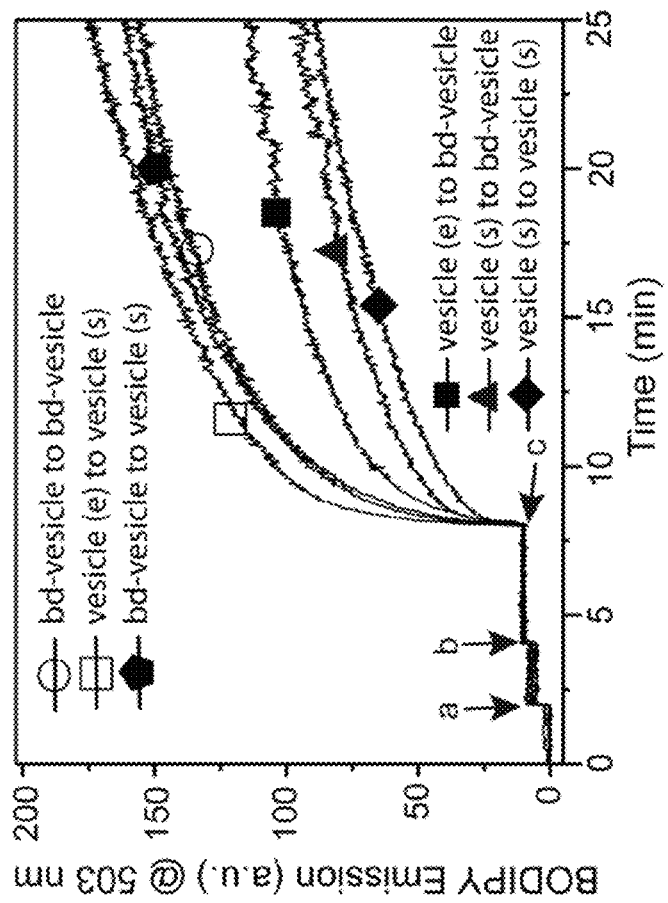

FIG. 12
(A)
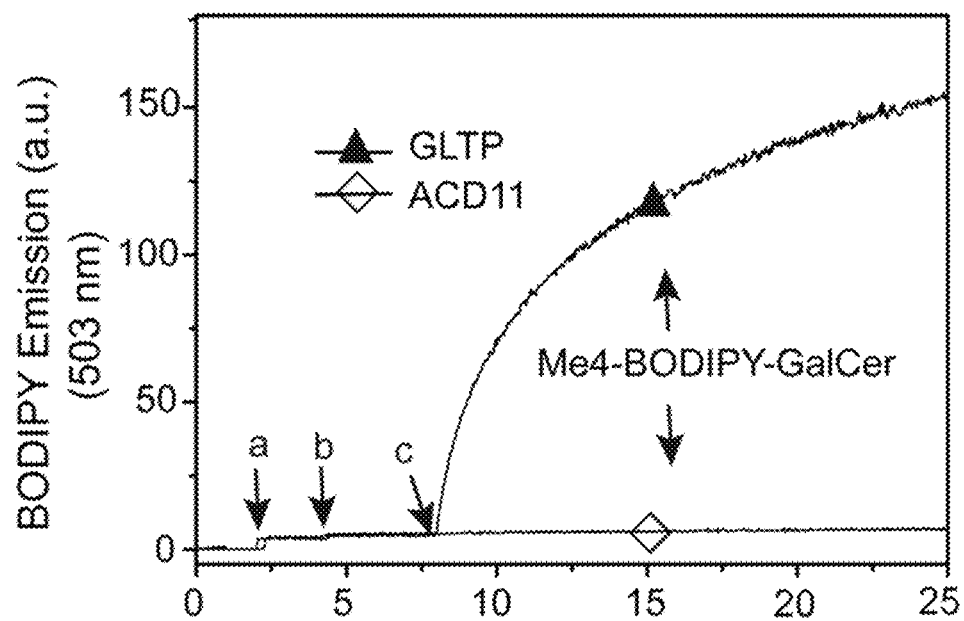
(B)
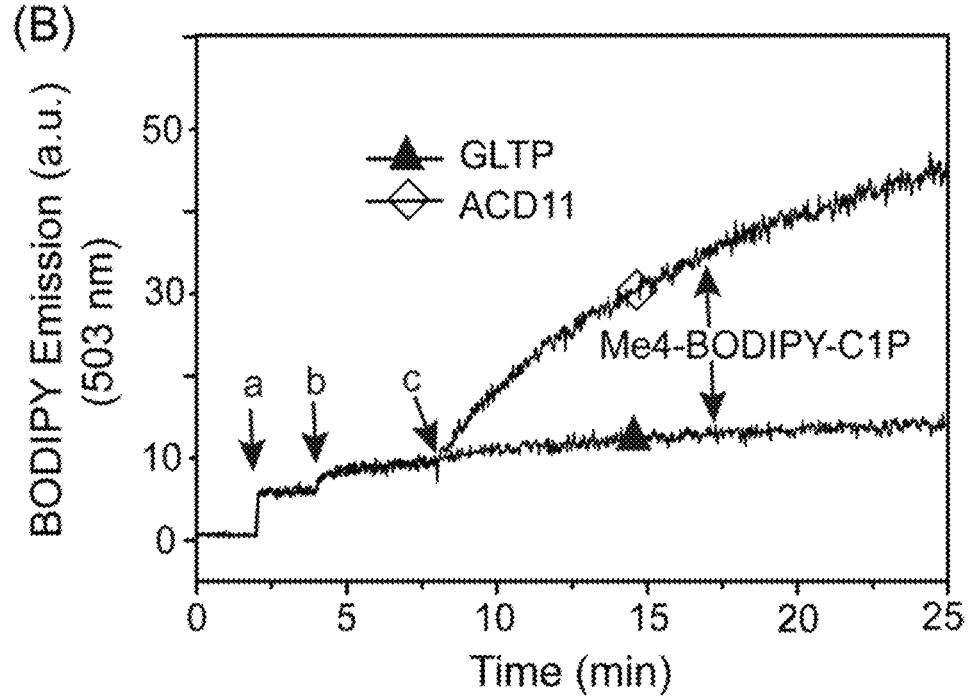

Fig 16
(A)
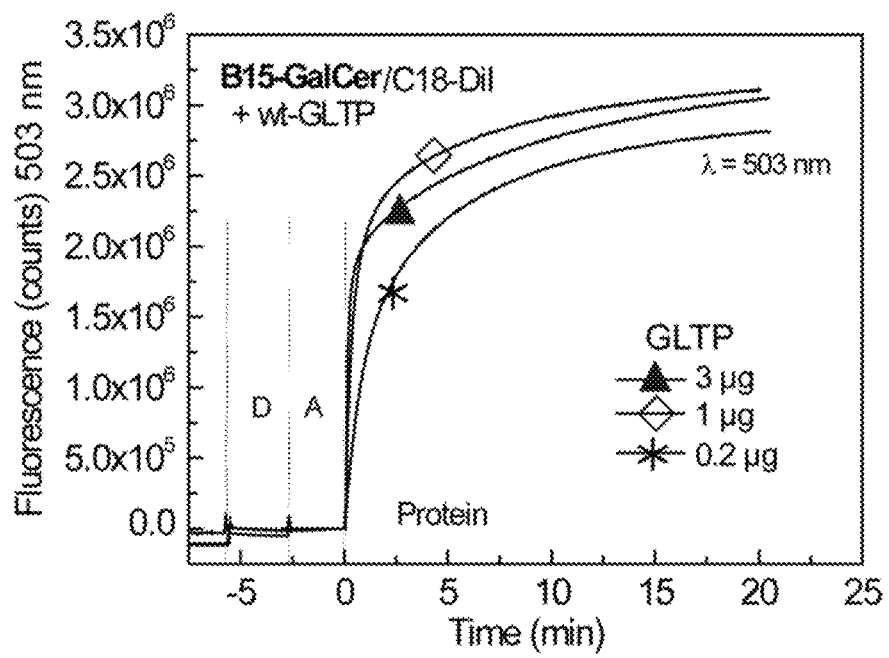
(B)
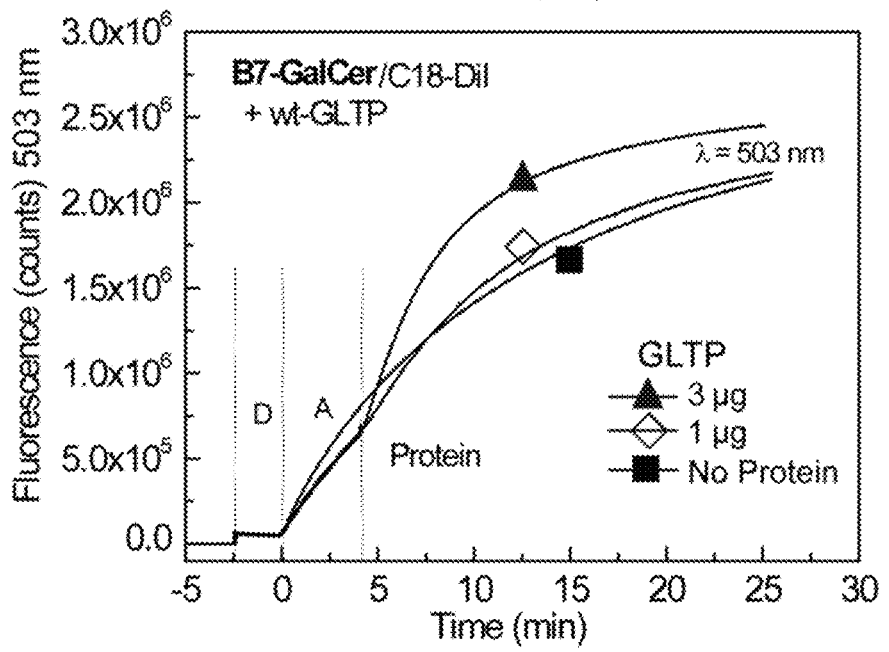

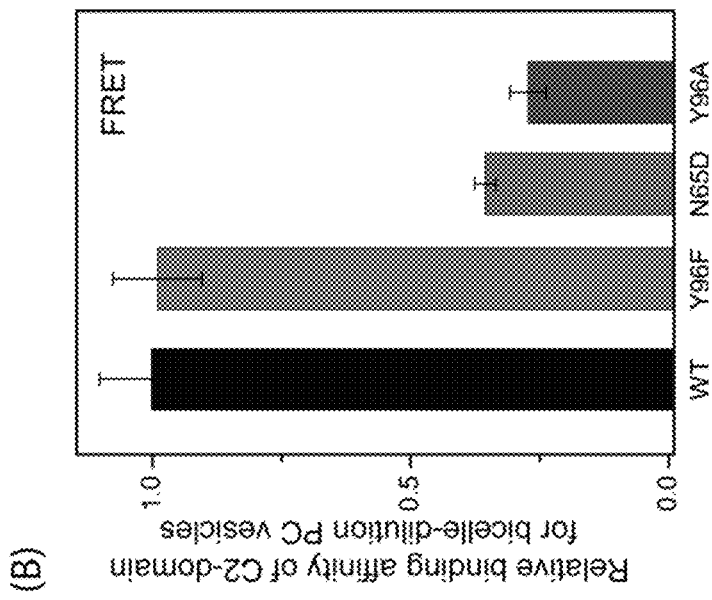
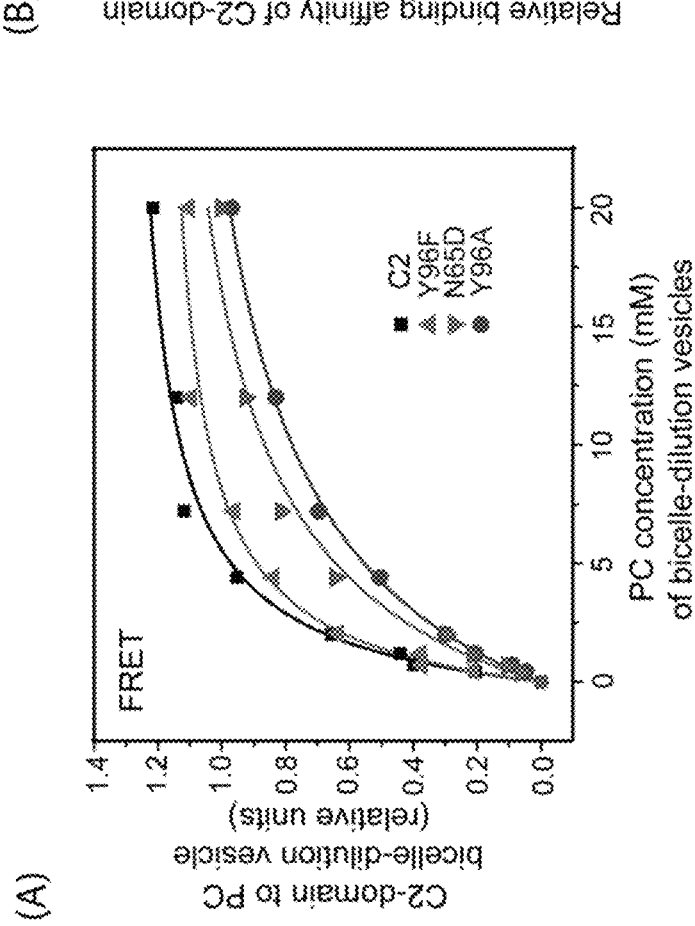
FIG. 19

MODEL-MEMBRANE-BASED LIPID TRANSFER ASSAYS AND METHODS

CROSS-REFERENCE TO RELATED APPLICATION

This application claims the benefit of U.S. Provisional Patent Application No. 62/890,238, filed Aug. 22, 2019, which is incorporated herein by reference in its entirety.

GOVERNMENT FUNDING

This invention was made with government support under HL125353 and GM045928 awarded by the National Institutes of Health. The government has certain rights in the invention.

SUMMARY

This disclosure describes, in one aspect, an assay system for measuring transfer of lipid from a donor model biomembrane to an acceptor model biomembrane. Generally, the system includes a donor model biomembrane that has a lipid with a detectable label, a lipid transfer protein that specifically binds the detectable lipid, and an acceptor model biomembrane. At least one of the donor model biomembrane and the acceptor model biomembrane is a bicelle-dilution model membrane.

In some embodiments, both the donor model biomembrane and the acceptor model biomembrane are bicelle-dilution model membranes.

In some embodiments, the bicelle-dilution membrane is a single-bilayer membrane vesicle that includes a generally planar lipid bilayer matrix. The lipid bilayer matrix includes two oppositely apposed layers of long-chain phosphoglycerides, the polar head groups of the long-chain phosphoglycerides forming an outer surface, the nonpolar tails of the long-chain phosphoglycerides arranged end-to-end with nonpolar tails of phosphoglycerides of the apposed layer forming a hydrophobic core. The lipid bilayer matrix further includes a stabilizing rim that includes a detergent or short-chain phosphoglycerides, the rim having a hydrophilic portion directed toward the hydrophobic core and a hydrophilic portion connects the first out surface with the second outer surface.

In some embodiments, the bicelle-dilution model membrane has a diameter of from 30 nm to 40 nm.

In another aspect, this disclosure describes a method of measuring lipid transfer between model membranes. Generally, the method includes providing any embodiment of the assay system summarized above, incubating the donor model biomembrane, the receptor model biomembrane, and the lipid transfer protein together under conditions effective to allow the lipid transfer protein to transfer the lipid from the donor model biomembrane to the receptor model biomembrane, and detecting the lipid transferred to the receptor model biomembrane.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 8. Characterization of bicelle-dilution model membranes used in Lipid Transfer Protein (LTP) assay by cryo-electron microscopy (cryo-EM). (A) Cryo-EM of 0.5 q-value dilution POPC/DHPC donors with FRET fluorophore lipids showing unilamellar nature and 31.5±3.8 nm outer diameter. (B) Bar graph shows vesicle size distribution resulting from dilution.

FIG. 9. Characterization of bicelle-dilution model membranes used in LTP assay. (A) Cryo-EM of 0.5 q-value dilution POPC/DHPC acceptors showing unilamellar nature and 36.3±6.1 nm outer diameter. (B) Bar graph shows vesicle size distribution resulting from dilution.

FIG. 10. Bicelle-dilution LTP assay robustness. (A) GLTP accessibility to BODIPY-GalCer indicates bicelle-dilution (bd)-vesicles are stable and unilamellar. (B) Lack of dilution-induced structure changes to POPC/DHPC model membranes during the assay time course. 0.5 q-value donors (a) were mixed with 0.5 q-value acceptors (b) and equilibrated for various time intervals prior to GLTP addition (c).

FIG. 11. Bicelle-dilution LTP assay robustness. (A) Effects of different combinations of bd-vesicles versus conventional small unilamellar vesicle (SUV) donors and acceptors on GLTP transfer activity. Vesicles (s)=sonicated small vesicles; vesicles (e)=ethanol-injection small vesicles; donor and acceptor q-value mix=0.5. (B) Superior stability of bd-vesicles improves FRET lipid transfer assay performance compared to conventional vesicles. Donors prepared in different ways were used in the transfer assay either soon after preparation or subjected to three freeze-thaw cycles (20° C. to −20° C.) prior to use. a=donors added (bd-vesicles or ethanol-injection vesicles), b=acceptors added (bd-vesicles or sonicated vesicles), and c=GLTP added.

FIG. 12. Detection of lipid specificity by different transfer proteins with the bicelle-dilution model membrane assay (Donor: q=0.5; Acceptor: q=0.5). (A) BODIPY-GalCer transfer by GLTP but not by ACD11 a plant ceramide-1-phosphate (C1P) transfer protein (CPTP). (B) BODIPY-C1P transfer by ACD11 but not by GLTP.

FIG. 16. Slow and physiologically relevant spontaneous transfer of Me$_4$-BODIPY-GalCer occurs when the linker chain for Me$_4$-BODIPY is long. (A) FRET measurements performed with GLTP using GalCer with Me$_4$-BODIPY linked via a pentadecanoyl chain. (B) FRET measurements performed with GLTP using GalCer with Me$_4$-BODIPY linked via a heptanoyl chain. Donors, acceptors, and GLTP additions are indicated by D and A.

FIG. 19. Use of bicelle-dilution vesicles for assessing protein binding to membranes. (A) FRET-binding isotherms showing the POPC-DHPC bicelle-dilution vesicle dependence of point mutant and control protein (0.5 mM) equilibrium adsorption at 50 mM $Ca^{2+}$. (B) Relative binding affinity of C2-domain point mutants and control protein obtained for binding isotherms shown in (A). The point mutants involve an interaction site in the C2-domain that is specific for the polar head group of phosphatidylcholine.

DETAILED DESCRIPTION OF ILLUSTRATIVE EMBODIMENTS

Figure 1:
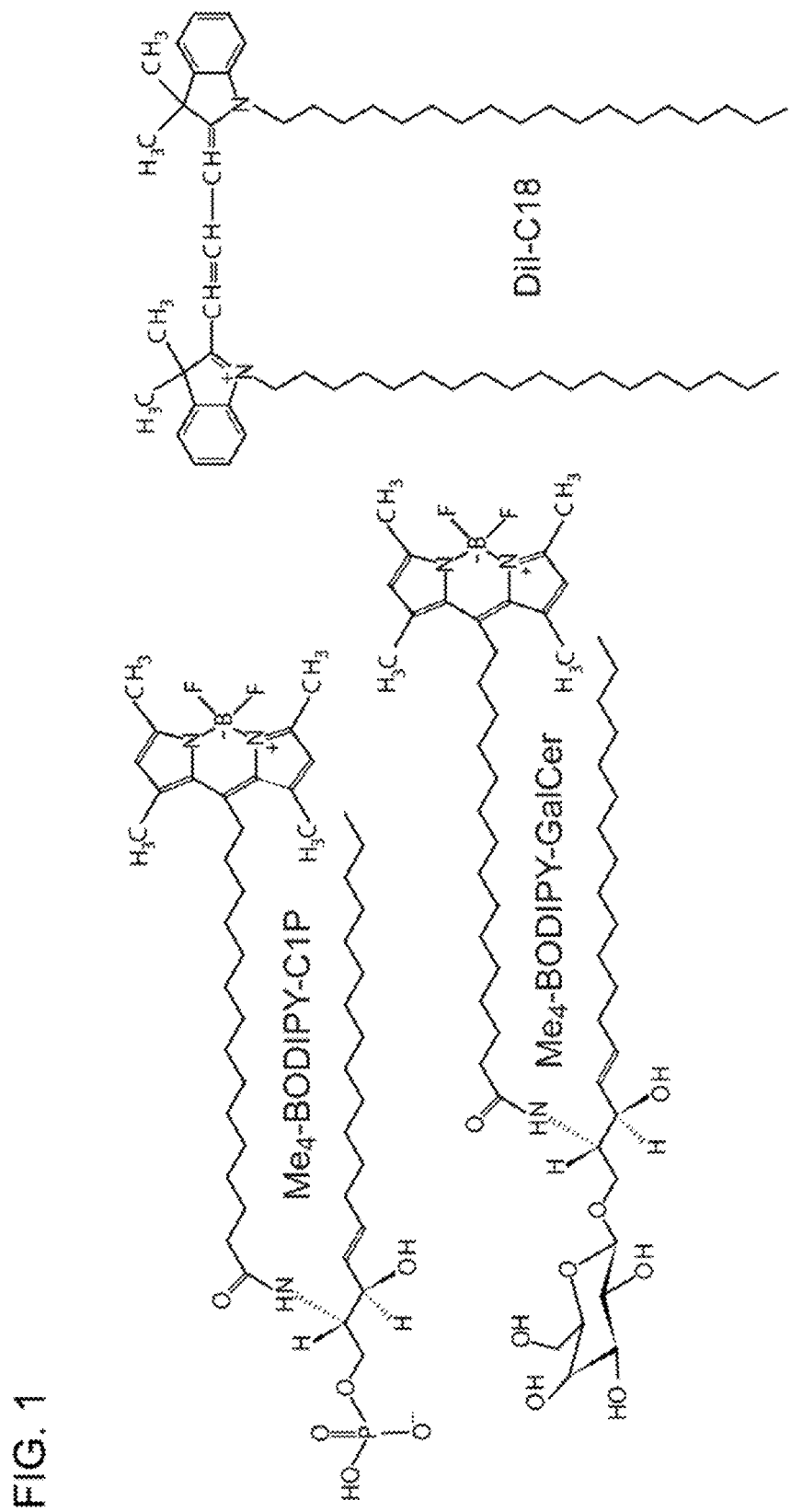
FIG. 1. Bicelle-Dilution-Model-Membrane-based lipid transfer measurement by lipid transfer proteins using Fluorescence Resonance Energy Transfer (FRET). Structures FRET energy donors ($Me_4$-BODIPY-GalCer, $Me_4$-BODIPY-C1P) that can be transferred by GLTP and CPTP, respectively, and nontransferable FRET energy acceptor (C18-diI).

Lipids provide the basic structural platform for membrane bilayers that surround and internally compartmentalize cells in various eukaryotic tissues. Cells rely on nonvesicular lipid transport to help regulate lipid metabolic and recycling processes involved in maintaining membrane integrity during, for example, periods of cell growth and proliferation. Nonvesicular lipid transport is performed by lipid transfer proteins (LTPs) that have the ability to bind and transfer specific lipids between membranes. LTPs are amphitropic proteins that that use their lipid-specific binding sites to acquire and release lipid cargo during transient interactions with membranes. When bound, the lipid cargo is sufficiently shielded from the cellular aqueous milieu so that LTPs effectively become molecular solubilizers of lipid.

Current approaches for assaying lipid intermembrane transfer typically rely on phospholipid bilayer vesicles prepared by sonication, ethanol-injection, or extrusion. One must freshly prepare vesicles for use in lipid transfer assays to avoid post-preparation, storage-related changes that affect vesicle size uniformity and/or aggregation state. Such changes can decrease the precision, reliability, and/or reproducibility of lipid transfer assays.

This disclosure describes the use of model membranes generated by bicelle dilution, referred to herein as bicelle-dilution model membranes, as model membranes for evaluating lipid transfer protein activity. As used herein, the term "model membrane" includes both bicelles and vesicles. Small vesicles are typically unilamellar—i.e., single-bilayer spheres. Thus, as used herein, the terms bicelle-dilution model membrane (b-d model membrane) and bicelle-dilution vesicle (b-d vesicle) refers to small and homogeneous single-walled bilayer model membranes that spontaneously form upon dilution (>100-fold) of a bicelle preparation in an aqueous medium. One feature of b-d model membranes described herein is placement of more lipid surface in the outer-most surface where it is accessible to lipid transfer proteins, which cannot penetrate through the lipid bilayer.

In contrast, a "conventional" model membrane (e.g., a conventional vesicle, a conventional micelle, or a conventional nanodisc) is a model membrane that are prepared using conventional methods.

The bicelle-dilution model membranes described herein can have a diameter of from 10 nm to 60 nm, although in certain embodiments the b-d model membranes can have a diameter outside of this range. In some embodiments, a b-d model membrane can have a minimum diameter of at least 10 nm such as, for example, at least 20 nm, at least 25 nm, at least 30 nm, or at least 35 nm. In some embodiments, a b-d model membrane can have a maximum diameter of no more than 60 nm such as, for example, no more than 50 nm, no more than 45 nm, or no more than 40 nm.

In some embodiments, a b-d model membrane can have a diameter that falls within a range having endpoints defined by any minimum diameter listed above and any maximum diameter listed above hat is greater than the minimum diameter. Thus, a b-d model membrane can have a diameter of 30 nm to 40 nm such as, for example, 35 nm to 40 nm.

In certain embodiments, a b-d model membrane can have a diameter that is equal to any minimum diameter or any maximum diameter listed above. Thus, for example, a b-d model membrane can have a diameter of 30 nm, 35 nm, or 40 nm.

Figure 4:
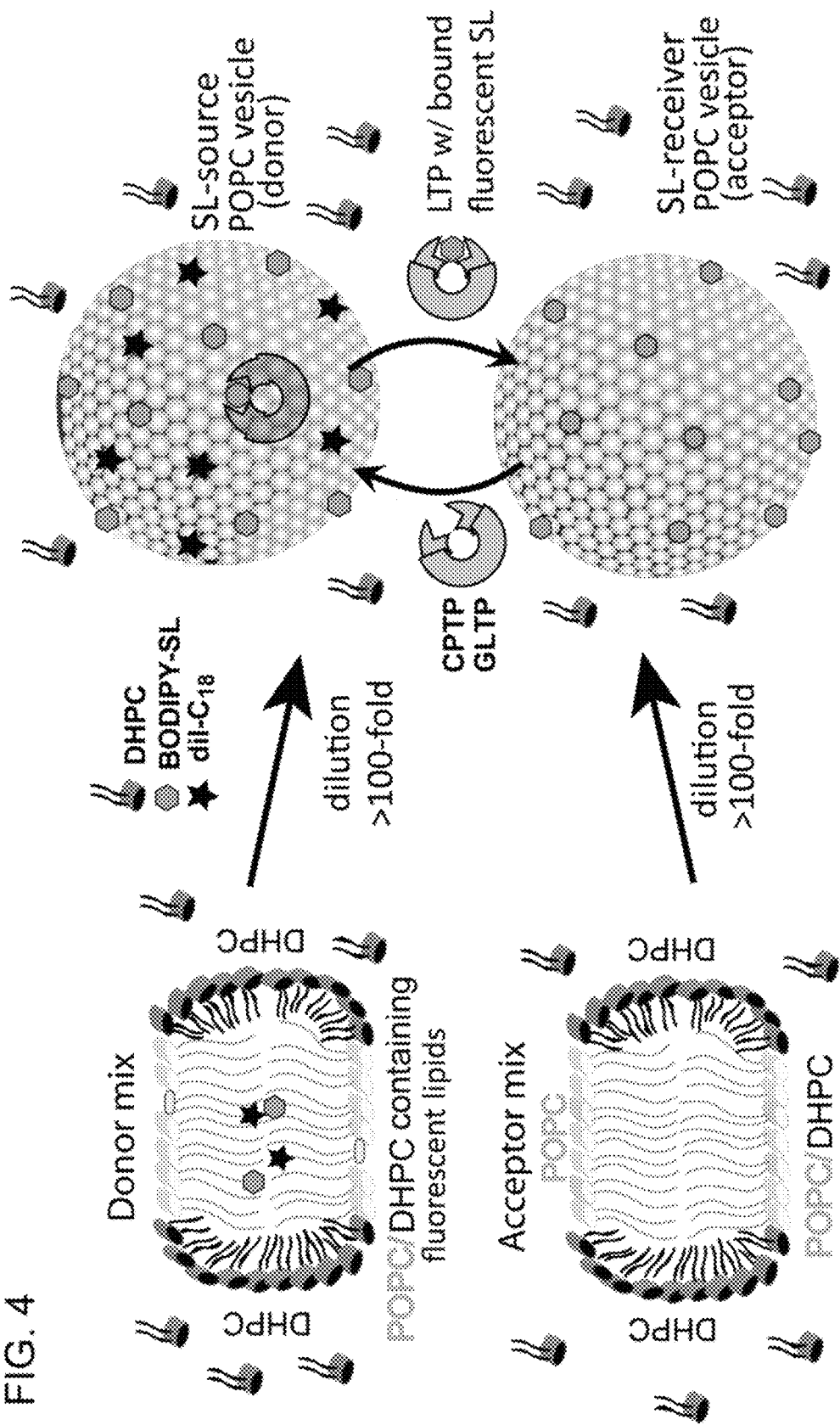
FIG. 4. Schematic depiction of model membrane vesicle formation by dilution of POPC/DHPC bicelles and GLTP-mediated transfer of $Me_4$-BODIPY-GalCer (lime green fluorophore) out of POPC/DHPC bicelle-dilution donor vesicles containing nontransferable C18-diI (red) to POPC/DHPC acceptor bicelle-dilution vesicles. Bicelles are disc-shaped assemblies shown in cross-section. Vesicles are membrane spheres with only the outer surface phospholipid polar head groups shown. Bicelles and vesicles not drawn to scale.

Bicelles and bicelle-dilution model membranes, are illustrated schematically in FIG. 4. Bicelles are lipid aggregates that self-assemble in aqueous environments to form disc-like structures consisting of flat bilayer-like core regions and curved micelle-like edge regions (FIG. 4, left-side structures). The planar bilayer core is formed by long-chain phosphoglyceride (illustrated in FIG. 4. as POPC, 1-palmitoyl-2-oleoyl phosphatidylcholine) whereas the curved rim consists of detergent or short-chain phosphoglyceride (illustrated in FIG. 4 as DHPC, dihexanoyl phosphatidylcholine) that shields the long-chain lipid tails from water. Bicelle-dilution model membranes—i.e., small (35-40 nm diameter) single-wall bilayer vesicles (illustrated in FIG. 4, right-side structures)—form spontaneously upon large dilution of bicelles (>100-fold) into an aqueous medium under our experimental conditions.

In both bicelles and bicelle-dilution model membranes, the long-chain phosphoglycerides in the bilayer-like core region can be homogenous or a mixture of suitable long-chain phosphoglycerides. In bicelles but not bicelle-dilution model membranes, the short-chain phosphoglycerides forming the rim can be homogenous or a mixture of suitable short-chain phosphoglycerides and/or detergents.

As used herein, a long-chain phosphoglyceride is a phosphoglyceride having a carbon chain of at least nine carbons. For example, the minimum carbon chain length for forming a bilayer is nine ($C_9$) for phosphatidylcholine (PC), $C_9$ for phosphatidylserine (PS), and $C_{11}$ for phosphatidylglycerol (PG). Biologically, lipid chain lengths rarely exceed 26 hydrocarbons. However, in some embodiments, the long-chain phosphoglyceride is can be chemically synthesized and may not necessarily adhere to maximum hydrocarbon lengths observed in natural biological settings. In some embodiments, the long-chain phosphoglyceride can have a maximum hydrocarbon length of no more than 26 carbons ($C_{26}$), no more than 20 carbons ($C_{20}$), no more than 19 carbons ($C_{19}$), no more than 18 carbons ($C_{18}$), no more than 17 carbons ($C_{17}$), no more than 16 carbons ($C_{16}$), no more than 15 carbons ($C_{15}$), no more than 14 carbons ($C_{14}$), no more than 13 carbons ($C_{13}$), or no more than 12 carbons ($C_{12}$).

Exemplary long-chain phosphoglycerides include, but are not limited to, 1-palmitoyl-2-oleoyl phosphatidylcholine (POPC); 1,2-dimyristoyl-sn-glycero-3-phosphocholine (DMPC or D14PC); 1,2-dilauryl-sn-glycero-3-phosphocholine (DLPC or D12PC); 1,2-dipalmitoyl-sn-glycero-3-phosphocholine (DPPC or D16PC); 1,2-distearoyl-sn-glycero-3-phosphocholine (DSPC or D18PC); 1,2-diarachidoyl-sn-glycero-3-phosphocholine (DAPC or D20PC); other phosphatidylcholines containing various combinations of long saturated or unsaturated acyl chains equal to or greater than 12 hydrocarbons in length; egg sphingomyelin (ESM); milk sphingomyelin (MSM); N-oleoyl sphingomyelin (18:1 SM); other sphingomyelins containing various long saturated or unsaturated acyl chains equal to or greater than 12 hydrocarbons in length; combinations of a phosphatidylcholine and a sphingomyelin mixtures (e.g., POPC/MSM (1:1 POPC:MSM)); 1-tetradecanoyl-2-(4-(4-biphenyl)butanoyl)-sn-glycero-3-PC (14:0-04:0 (biphenyl) PC; TBBPC); 1,2-dimyristoyl-sn-glycero-3-phospho-(1'-rac-glycerol) (DMPG; di-14:0 PG); 1,2-dimyristoyl-sn-glycero-3-phospho-L-serine (DMPS; di-14:0 PS); 1-palmitoyl-2-oleoyl-sn-glycero-3-phospho-(1'-rac-glycerol) (POPG); 1-palmitoyl-2-oleoyl-sn-glycero-3-phospho-L-serine (POPS); 1,2-dimyristoyl-3-trimethylammonium-propane (14:0 TAP); 1,2-dimyristoyl-sn-glycero-3-ethylphosphocholine; (14:0 EPC); 1,2-di-O-dodecyl-sn-glycero-3-phosphocholine (12:0 diether PC); 1,2-di-O-tridecyl-sn-glycero-3-phosphocholine (13:0 diether PC); 1,2-di-O-tetradecyl-sn-glycero-3-phosphocholine (14:0 diether PC); 1,2-di-O-tetradecyl-sn-glycero-3-phospho-(1'-rac-glycerol) (14:0 diether PG); dimethyldioctadecylammonium (Bromide Salt) (18:0 DDAB); 1,2-dimyristoyl-sn-glycero-3-phosphoethanolamine-N-diethylenetriaminepentaacetic acid (14:0 PE-DTPA); 1,2-dimyristoyl-sn-glycero-3-phosphoethanolamine-N-diethylenetriaminepentaacetic acid (gadolinium salt) (14:0 PE-DTPA (Gd)); 1,2-dimyristoyl-sn-glycero-3-phosphoethanolamine-N-diethylenetriaminepentaacetic acid (copper salt) (14:0 PE-DTPA(Cu)).

As used herein, a suitable short-chain phosphoglyceride for the curved micelle-like edge region of a bicelle-dilution model membrane is a phosphoglyceride having a carbon chain short enough that the phosphoglyceride does not form a bilayer. The precise hydrocarbon length can therefore vary depending, at least in part, on whether the short-chain phosphoglyceride possesses two short chains (e.g., a dihexanoyl-PC) or a single long-chain phosphatidylcholine commonly known as lyso-PC. In some embodiments, the short-chain phosphoglyceride has two short chains having a maximum hydrocarbon length of no more than eight for phosphatidyl choline (di-C8-PC), no more than eight for phosphatidylserine (di-C8-PS), and no more than 10 for phosphatidylglycerol (di-C10-PG).

Exemplary suitable short-chain phosphoglycerides include, but are not limited to, two-chain phosphoglycerides such as, for example, dihexanoyl phosphatidylcholine (DHPC); 1,2-dipentanoyl-sn-glycero-3-phosphocholine (DSPC); 1,2-diheptanoyl-sn-glycero-3-phosphocholine (D7PC); 1,2-octanoyl-sn-glycero-3-phosphocholine (DSPC); and 1,2-di-O-hexyl-sn-glycero-3-phosphocholine; (6:0 Diether PC). Exemplary short-chain phosphoglycerides also include, but are not limited to, monochain phosphoglycerides such as, for example, an alkylphosphocholine (e.g., dodecylphosphocholine (12PC); tetradecylphosphocholine (14PC); hexadecylphosphocholine (16PC); octadecylphosphocholine (18PC); an odd-chain-length alkylphosphocholine ($C_{11}$, $C_{13}$, $C_{15}$, $C_{17}$); 6-cyclohexyl-1-hexylphosphocholine (cyclofos-6); 4-cyclohexyl-1-butylphosphocholine (cyclofos-4); 5-cyclohexyl-1-pentylphosphocholine (cyclofos-5); and 7-cyclohexyl-1-heptylphosphocholine (cyclofos-7)).

Exemplary suitable detergents for use in the curved micelle-like edge region of a bicelle-dilution model membrane include, but are not limited to, 3-[(3-cholamidopropyl)dimethyl-ammonio]-2-hydroxy-1-propanesulfonate (CHAPSO); 3-[(3-cholamidopropyl)dimethyl-ammonio]-1-propanesulfonate (CHAPS); sodium cholate; sodium glycocholate; sodium taurocholate; 3α-hydroxy-7α,12α-di-((O-β-D-maltosyl)-2-hydroxyethoxy)-cholane (Façade-EM); 3α-hydroxy-7α,12α-di-((2-(trimethylamino)ethyl)phosphoryl)ethyloxy)-cholane (Façade-EPC); a styrene/maleic acid (SMA) copolymer; or a synthetic (non-natural) detergent.

Bicelles have been used as bilayer platforms to study the structure of embedded integral proteins by NMR. Neither bicelles nor bicelle-dilution model membranes have previously been used to study lipid transfer reactions mediated by proteins that selectively transfer specific lipids embedded in these model membranes.

This disclosure describes assay systems in which lipid transfer between model membrane is monitored using established fluorescence resonance energy transfer (FRET) technology. FRET-based lipid transfer assays are well established for tracking the transfer of specific lipids between membrane vesicles by various lipid transfer proteins (LTPs)—e.g., the transfer of sphingolipids by glycolipid transfer protein (GLTP) and by other GLTP superfamily members. This disclosure describes bicelle-dilution-model-membrane-based lipid transfer assay systems, characterizes conditions for the effective use of these assay systems, and demonstrates advantages of using bicelle-dilution model membranes compared to bilayer vesicles for in vitro monitoring of fluorescent lipid transfer reactions. This disclosure describes an exemplary embodiment of the new approach that involves monitoring the transfer of specific sphingolipids between membrane vesicles by glycolipid transfer protein (GLTP) and by other GLTP superfamily members.

FRET Approach for Tracking Lipid Intermembrane Transfer

Figure 2:
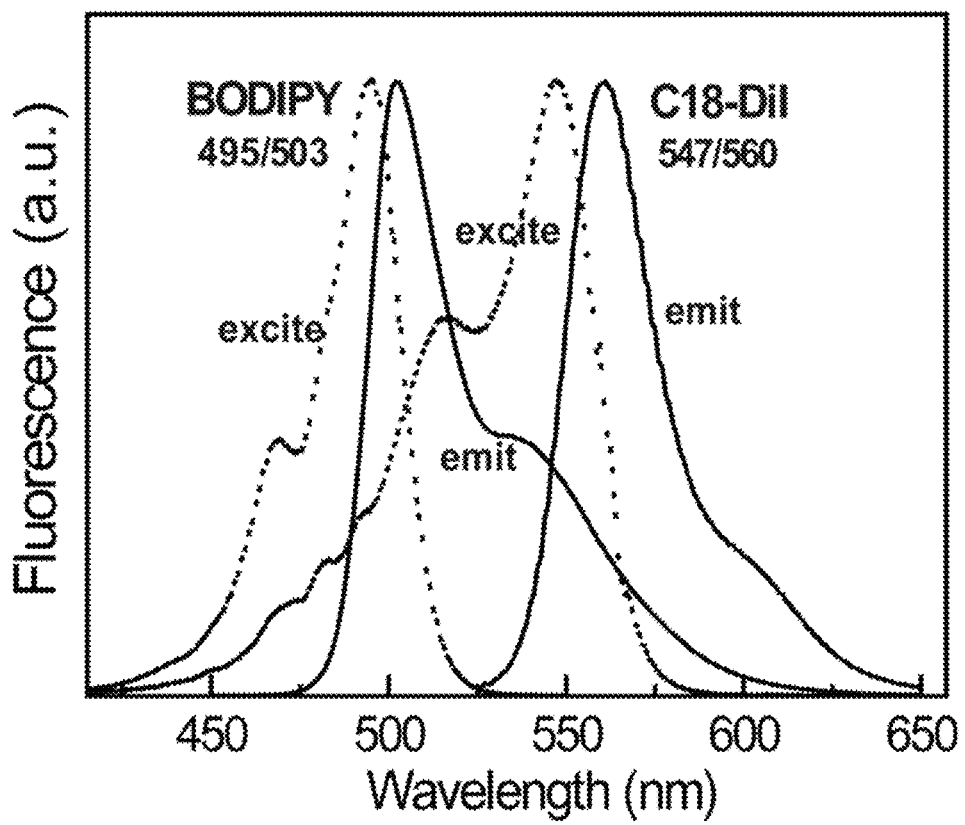
FIG. 2. Bicelle-Dilution-Model-Membrane-based lipid transfer measurement by lipid transfer proteins using Fluorescence Resonance Energy Transfer (FRET). Excitation and emission spectra of $Me_4$-BODIPY-SL and C18-diI incorporated into bicelle-dilution model membranes.
Figure 3:
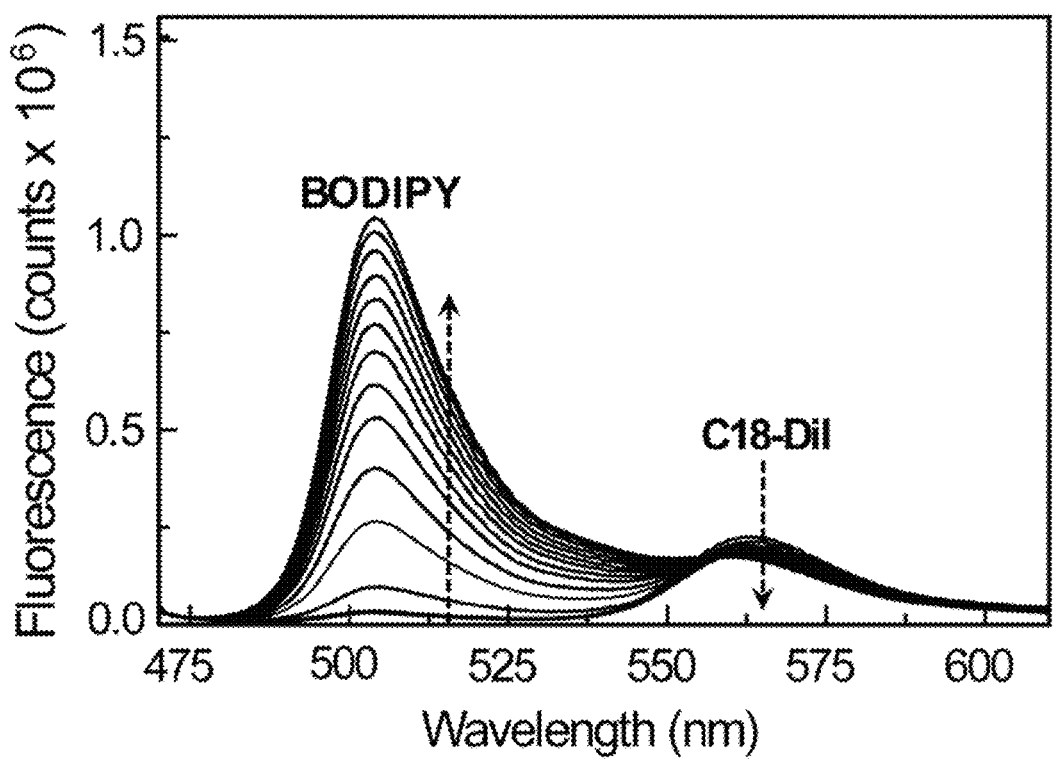
FIG. 3. Time-based response of B15-GalCer/C18-Dil after wt-GLTP addition. FRET emission changes observed upon mixing donor bicelle-dilution model membranes formed by diluting POPC/DHPC donor bicelles containing $Me_4$-BODIPY-GalCer and C18-diI with excess acceptor model membranes formed by diluting POPC/DHPC bicelles followed by GLTP.

Compared to many other fluorophores, boron dipyrromethane (BODIPY, 4,4-difluoro-4-bora-3a,4a-diaza-s-indacene) exhibits photo-physical properties that enhance lipid transfer assay performance—i.e., high environmental stability, high photo-stability, low environmental polarity sensitivity, and high emission intensity. For these reasons, sphingolipid (SL) carrying a pentadecanoyl acyl chain labeled with tetramethyl-BODIPY ($Me_4$-BODIPY) was used as energy donor and $C_{18}$-diI as energy acceptor for real-time kinetic tracking of the complete lipid transfer reaction using fluorescence resonance energy transfer (FRET) technology, which provides an order of magnitude sensitivity increase compared to the anthrylvinyl-SL/-3-perylenoyl-PC energy donor/acceptor pair previously used to track lipid transfer. The complete lipid transfer reaction involves uptake of sphingolipid (SL) by protein from an SL-source (donor) model membrane and delivery of sphingolipid by protein to a receiver model membrane (acceptor). FIG. 1 illustrates exemplary lipid fluorophore structures. FIG. 2 and FIG. 3 show changes in FRET response that reflect sphingolipid transfer. Wavelength-selective excitation of $Me_4$-BODIPY-SL initially results in minimal emission, but strong emission by $C_{18}$-diI via FRET due to the close proximity of both fluorescent lipids in SL-donor (source) model membranes. Addition of excess acceptor (receiver) model membranes (containing no lipid fluorophores) and sphingolipid-specific transfer protein (SLTP) triggers a sudden and time-dependent emission increase by $Me_4$-BODIPY sphingolipid due to the loss of FRET resulting from fluorescent sphingolipid transfer that creates separation from nontransferable $C_{18}$-diI.

Figure 5:
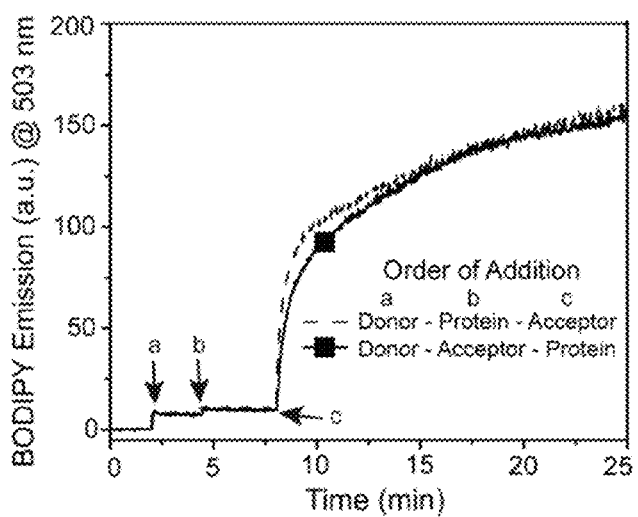
FIG. 5. Glycolipid transfer protein (GLTP) addition prior to adding acceptor bicelle-dilution model membranes does not affect BODIPY-lipid transfer activity. FRET changes reflect BODIPY-lipid transfer between donor and acceptor model membranes, not BODIPY-lipid binding by lipid transfer protein (GLTP). For black trace, a=donors added, b=acceptors added, and c=GLTP added. For red trace, a=donors added, b=GLTP added, and c=acceptors added. Response signals are nearly identical.
Figure 6:
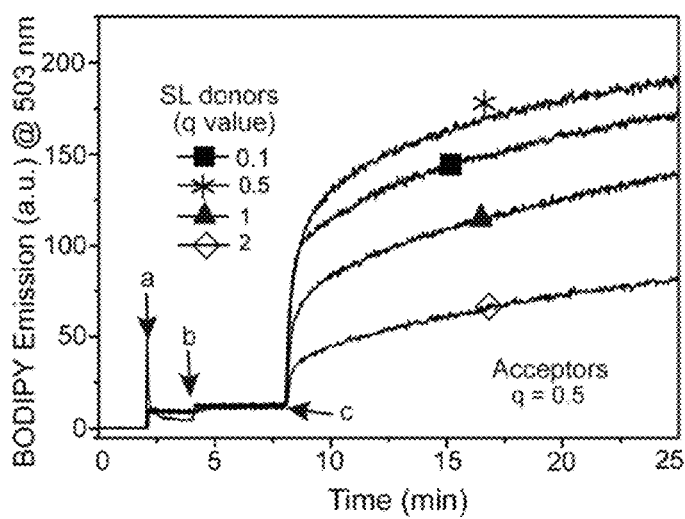
FIG. 6. Effect of different q-values for donor bicelle-dilution model membranes on transfer activity of GLTP. Donor model membrane q-values: 0.1, 0.5, 1, or 2; Acceptor model membrane: q-value=0.5.
Figure 7:
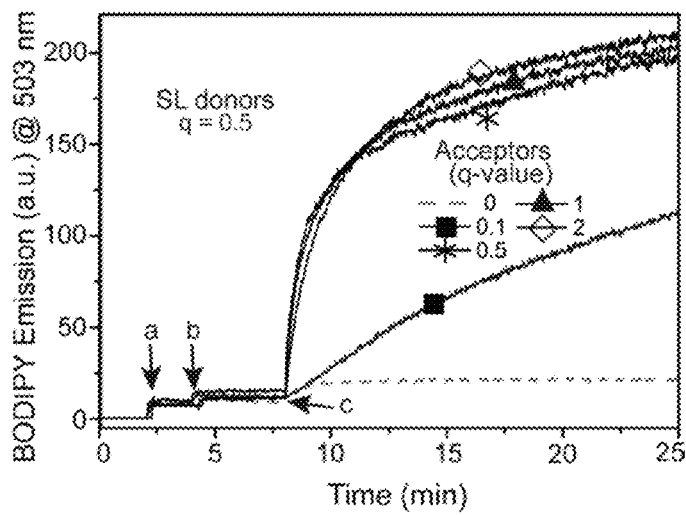
FIG. 7. Effect of different q-values for acceptor bicelle-dilution model membranes on transfer activity of GLTP. Donor model membranes: q-value=0.5; Acceptor model membranes q-values: 0, 0.1, 0.5, 1, or 2. Donor q-value= (POPC+BODIPY-GalCer)/DHPC; Acceptor q-value= (POPC/DHPC).

Use of Bicelle-Dilution Model Membranes for Tracking Lipid Intermembrane Transfer Using the preceding FRET approach, the extent to which bicelle-dilution model membranes (FIG. 4) can serve as suitable model membranes for determining the complete sphingolipid transfer reaction mediated by sphingolipid lipid transfer proteins was assessed. FIGS. 5-7 show protein loading with sphingolipid from donor bicelle-dilution model membranes followed by sphingolipid delivery to acceptor b-d model membranes. Initially, b-d model membranes with a q-value of 0.5 were tested because of their well-characterized properties and established suitability for high-resolution solution-state NMR studies involving the structure and dynamics of membrane-associated peptides. Q-value refers to the molar ratio of long-chain phosphatidylcholine to detergent used to construct the b-d model membranes. Adjustment of the q-value alters the discoidal size of b-d model membranes. Bicelle-dilution model membranes formed by POPC and DHPC were selected to favorably accommodate BODIPY-labeled sphingolipid and $C_{18}$-DiI.

As shown in FIG. 5, SL-donor and acceptor model membranes formed by 0.5 q-value b-d model membrane mixtures support robust sphingolipid transfer. Almost no increase in BODIPY-SL emission occurs between the SL-donor b-d model membranes and excess acceptor b-d model membranes until transfer protein is added, confirming very slow spontaneous sphingolipid migration to acceptor b-d model membranes. Also, combining SL-donor b-d model membranes with only protein fails to significantly increase BODIPY-SL emission unless followed by addition of acceptor b-d model membranes, showing that protein binding of BODIPY-SL does not explain the FRET response. Rather, the low "catalytic" amounts of GLTP act in shuttle-like fashion to transfer $Me_4$-BODIPY-GalCer continuously from the SL-donor b-d model membranes to the excess acceptor b-d model membranes until dynamic equilibrium is reached (~20 minutes).

Figure 15:
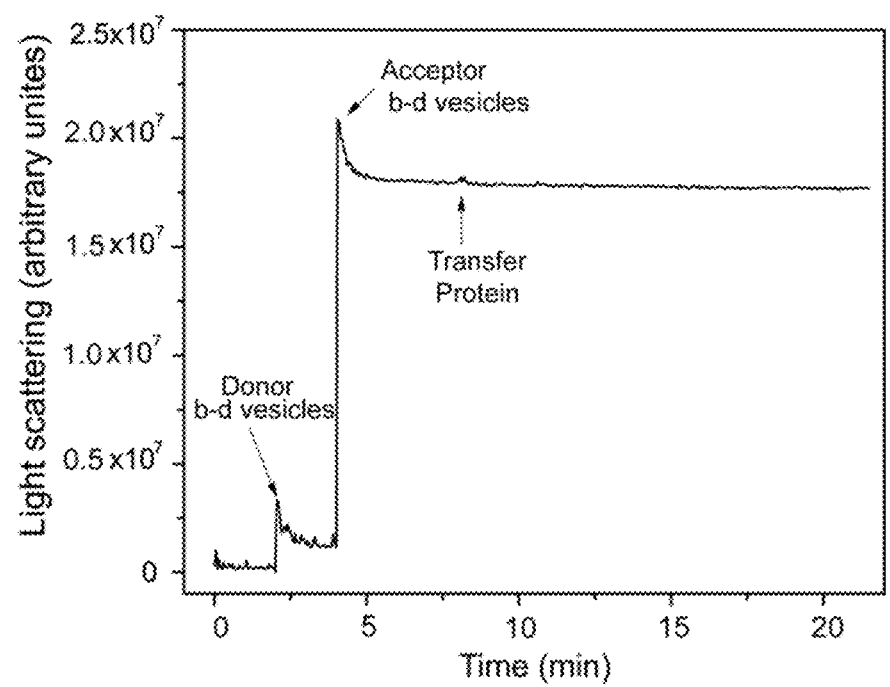
FIG. 15. Lack of size change due to fusion by donor and acceptor model membranes during LTP assay. 90° static light scattering intensity measured as a function of time under conditions bicelle-dilution assay conditions involving Me4-BODIPY-GalCer transfer by GLTP. Measurements were performed while irradiating at 320 nm and at 24° C. Arrows indicate the addition of bicelle-dilution donor vesicles (48 µM), bicelle-dilution acceptor vesicles (720 µM), and GLTP (~17 nM).

Next, the aggregation/fusion state of the donor and acceptor b-d model membranes were monitored by light scattering before and after GLTP was added. FIG. 15 shows that the 90° light scattering signal obtained after addition of donors, followed by acceptors (15×), and then GLTP, produced no changes, consistent with vesicle aggregation or fusion. Measurements were performed at 320 nm to avoid fluorescence contributions from the BODIPY and diI probes. Although the scattering intensity increased very abruptly with each addition of b-d model membranes due to the increased number of scattering objects (e.g., large jump with 15× acceptors; FIG. 15), the signal response stabilized rapidly and remained unchanged for several minutes. Addition of GLTP produced almost no signal change in scattering because of the 24 kDa protein's low concentration (~17 nM) relative to the ~75 kDa donor (48 µM) and acceptor (720 µM) bicelles. The unchanging scattering response over the time interval that coincides with large changes in FRET induced after protein addition rules out vesicle aggregation or fusion as the reason for the FRET signal change.

The very slow spontaneous transfer of BODIPY-SL between donor and acceptor b-d model membranes in the absence of transfer protein is observed only when the fluorophore is linked to the sphingolipid via a long, physiological-like aliphatic chain (FIG. 16A). When BODIPY is attached via a short nonphysiological linker chain, the spontaneous inter-b-d-model-membrane transfer rate for the $Me_4$-BODIPY-SL increases by several orders of magnitude (FIG. 16B).

As mentioned earlier, changing the q-value alters the size and form of b-d model membranes. In the low q-value range (<0.3), mixed micelles can result. Higher q-values (e.g., 1.0 and 2.0) lead to fewer b-d model membranes but with increased overall diameter—i.e., more bilayer core and proportionally less edge, compared to 0.5 q-value b-d model membranes at equivalent total lipid concentrations. To determine which q-values work best in the lipid transfer assay, SL-donors generated by dilution of various q-value mixtures were assessed when using 0.5 q-value acceptor b-d model membranes. FIG. 6 shows that a donor q-value of 0.5 resulted in faster sphingolipid transfer compared to donors formed using lower (0.1) or higher (1.0 or 2.0) q-values. FIG. 7 shows the effect of acceptor model membranes produced from different q-value mixtures on sphingolipid transfer rates using 0.5 q-value sphingolipid donors. Under these conditions, transfer decreased strongly when the acceptor q-value was 0.1, but not for acceptors with q-values of 1.0 and 2.0. Due to the preceding outcomes, further analyses on donor and acceptor b-d model membranes used b-d model membranes with q-values of 0.5.

Assay conditions for 0.5 q-value stock mixtures of donors and acceptors typically involve 125-fold dilution to the range of ~192 µM to 512 µM DHPC, well below its 14 mM critical micelle concentration (cmc), but not POPC (≈0.5 nM). In b-d model membranes, the high aqueous solubility of rim-stabilizing amphiphiles such as DHPC requires high total lipid concentrations (e.g., greater than 1-2 wt %) to maintain b-d model membrane structural stability. Dilution with aqueous buffer can trigger re-equilibration of DHPC into the aqueous phase to drive structural changes including bilayer vesicle formation. Modeling studies suggest a vesicle formation mechanism driven by bicelle coalescence resulting from DHPC loss from the rim. With more DHPC departure, the perimeter (rim) line tension begins to dominate the elastic bending energy, leading to cup-shaped vesicle intermediates that reduce hydrocarbon chain exposure to water. Eventual closure forms unilamellar vesicles.

To determine the nature of the stock model membranes formed from the 0.5 q-value mixtures, form and size of the model membranes were assessed. Cryo-electron microscopy (cryo-EM) imaging, which relies on ultra-rapid freezing, indicated formation of highly homogenous unilamellar vesicles by the 0.5 q-value dilution donors and acceptors (FIG. 8A and FIG. 9A). Donor vesicle diameters averaged 32±4 nm (FIG. 8B) and acceptor vesicle diameters averaged 36±6 nm (FIG. 9B). Negative-stain EM analyses provided similar size information although sample dehydration and osmotic stress artifacts appeared to promote vesicle aggregation and affect vesicle shape.

Further support for the unilamellar nature of the bicelle-dilution donor vesicles was obtained by testing BODIPY-SL accessibility to soluble GLTP (FIG. 10A). The BODIPY-GalCer transfer equilibrium by GLTP approaches ~70% for bicelle-dilution vesicles. This value represents the BODIPY-GalCer present in the donor vesicle outer surface and accessible to GLTP based on solubilization with excess Tween-20 dispersing and diluting the BODIPY and DiI lipid fluorophores to provide signal estimates for 100% transfer. The unequal BODIPY-SL distribution in the outer and inner surfaces reflects the well-known lipid transbilayer mass imbalance resulting from curvature of small bilayer vesicles. The findings are consistent with the vast majority of the bicelle-dilution vesicles being unilamellar.

The stability of the stock donor and acceptor vesicles upon dilution into the assay were tested by comparing different mixing equilibration times prior to assay initiation by protein addition. FIG. 10B shows that introduction of GLTP at different time intervals after the initial mixing of POPC/DHPC bicelle-dilution SL donors and POPC/DHPC acceptors had minimal effect on the transfer kinetics of Me$_4$-BODIPY-SL. Moreover, after combining all assay components, no detectable change in 90° static light scattering occurs over the experimental time course (FIG. 15). DLS measurements of the 0.5 q-value stock acceptors diluted to FRET assay conditions showed no change in vesicle size over a 20-minute interval. Similar dilution measurements with stock 0.5 q-value donors exceeded reliable detection limits for vesicle sizing by DLS. Altogether, the results indicate that the time course for the typical lipid transfer assay is sufficiently fast to avoid major structural changes to the vesicles formed by bicelle dilution during the time course of a typical assay.

Figure 17:
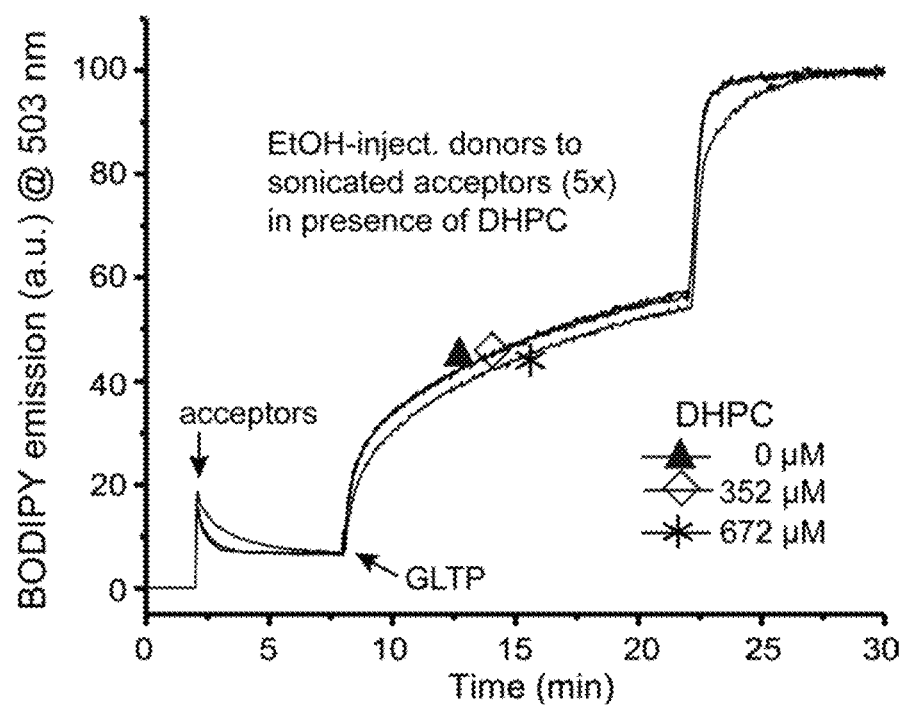
FIG. 17. Lack of significant effect by DHPC on Me$_4$-BODIPY-GalCer transfer by GLTP using ethanol-injection donors and sonicated acceptors (5×). The DHPC concentrations (352 µM and 672 µM) included in the assay buffer correspond to levels introduced when using 10-fold and 20-fold excess of bicelle-dilution stock acceptor vesicles.

SLTP Transfer Rates Achieved with b-d Model Membrane Vesicles Versus Conventional Small Vesicles Small phosphatidylcholine vesicles (25-40 nm diameters) have typically been used as model membranes to assess lipid inter-bilayer transfer because of the faster transfer rates compared to those obtained using larger vesicles. Different donor and acceptor combinations were tested involving either small vesicles and/or 0.5 q-value bicelle dilution vesicles (bd-vesicles) to determine which combination produced the fastest intermembrane transfer rates. FIG. 11A shows that bd-vesicle-to-bd-vesicle conditions result in fast sphingolipid transfer rates comparable with conventional vesicle-to-vesicle conditions so long as the donor vesicles are produced by rapid ethanol-injection rather than by sonication. When the donor vesicles were produced by sonication, sphingolipid transfer rates were markedly slowed regardless of whether the acceptors were bd-vesicles or sonicated vesicles. Using ethanol-injection donor vesicles in combination with 0.5 q-value bicelle acceptors resulted in intermediate sphingolipid transfer rates. Thus, similar high assay sensitivity can be achieved using the bicelle-to-bicelle transfer conditions as for vesicle-to-vesicle transfer conditions. In separate controls (FIG. 17), DHPC was included at similar and excess amounts as present when using bicelle-dilution vesicles. Minimal affect was detected in the GLTP transfer rate of Me$_4$-BODIPY-GalCer between ethanol-injection donors and sonicated acceptor vesicles.

Improved Storage Capacity of Bicelle-Dilution Vesicles Versus Conventional Small Vesicles The limited stability of membrane bilayer vesicle preparations results in a short shelf-life and typically imparts a need for fresh vesicle preparations to carry out high-quality lipid transfer assays. To determine if bd-vesicles exhibit superior stability and storage capacity compared to lipid vesicles prepared by other processes, resistance to freeze-thaw changes was tested. Freeze-thaw cycles can destabilize bilayer vesicles, thereby promoting aggregation and/or fusion of bilayer vesicles. In contrast, FIG. 11B shows the comparative effects of three freeze-thaw cycles on bd-vesicles or conventional vesicles prior to using them in the FRET lipid transfer assay. Me$_4$-BODIPY-GalCer transfer by GLTP was not affected by freeze/thawing of the bd-vesicles, whereas a significantly diminished transfer rate was observed with the vesicles. The findings indicate that the bd-vesicles can be prepared and then stored frozen prior to use without negatively affecting the assay system. In a separate control, stock bicelle-dilution vesicles kept at room temperature for up to six days did not negatively impact on their performance in the FRET assay (FIG. 10A).

Lipid Specificity for Different SLTPs

The GLTP superfamily consists of members with differing sphingolipid binding and transfer specificity. Whether bd-vesicle-to-bd-vesicle transfer conditions enable detection of the sphingolipid transfer specificity by different GLTP superfamily members was assessed. Whereas GLTP specifically transfers glycolipids such as galactosylceramide (GalCer), the CPTP plant ortholog, ACD11, specifically transfers only ceramide-1-phosphate (C1P). FIG. 12A shows that GLTP transfer of Me$_4$-BODIPY GalCer, but not Me$_4$-BODIPY C1P, is detected using bicelle donors and bicelle acceptors.

Similarly, FIG. 12B shows that the plant CPTP ortholog, ACD11, specifically transfers Me$_4$-BODIPY C1P, but not Me$_4$-BODIPY GalCer.

Assessment of Potential SLTP Inhibitors

Figure 13:
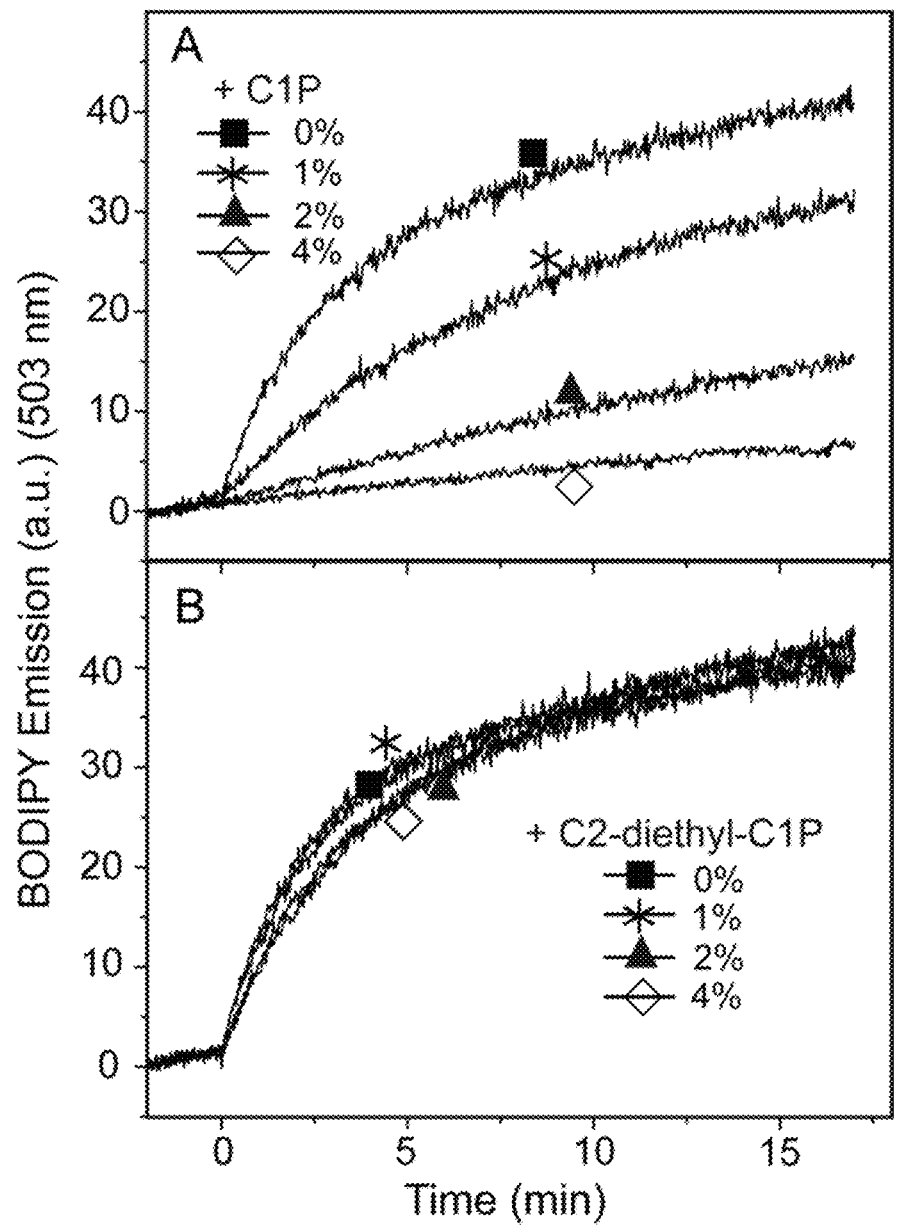
FIG. 13. Competitive inhibition of lipid-specific transfer in the bicelle-dilution model membrane assay. (A) Slowing of ACD11 transfer of BODIPY-C1P by increasing levels of nonfluorescent C1P indicates competition for interaction with ACD11. (B) Nonfluorescent diethyl-C1P fails to slow BODIPY-C1P transfer indicating no competition with BODIPY-C1P for interaction with ACD11 (i.e., no inhibition effect). (Donor: q=0.5; Acceptor: q=0.5).

The C1P derivative, diethyl-C1P, can inhibit cytosolic phospholipase A$_2$α (cPLA$_2$α) activity when the C1P acyl chain is short—e.g., C2-diethyl-C1P. The inhibition of cPLA$_2$α by C2-diethyl-C1P presumably occurs via interaction with the cPLA$_2$α C2-domain, which contains a C1P binding site that activates cPLA$_2$α by enhancing translocation to membranes. To date, no inhibitors of C1P transfer proteins (e.g., CPTP and ACD11) have been reported. The bicelle-dilution FRET assay was used to test whether C2-diethyl-C1P can inhibit the plant CPTP ortholog, ACD11. FIG. 13B shows that increasing concentrations of C2-diethyl-C1P in donor bicelles fail to exert a competition effect on ACD11-mediated transfer rates of Me$_4$-BODIPY C1P. In contrast, FIG. 13A shows that increasing concentrations of nonfluorescent C1P in donor bd-vesicles slow the interbicelles transfer rates. Despite the negative outcome for C2-diethyl-C1P, the data show the potential of the bicelle-dilution FRET assay for identifying as of yet undiscovered inhibitors for various lipid transfer proteins.

SLTP Activity and Specificity Detection Using Cell Lysate

Figure 14:
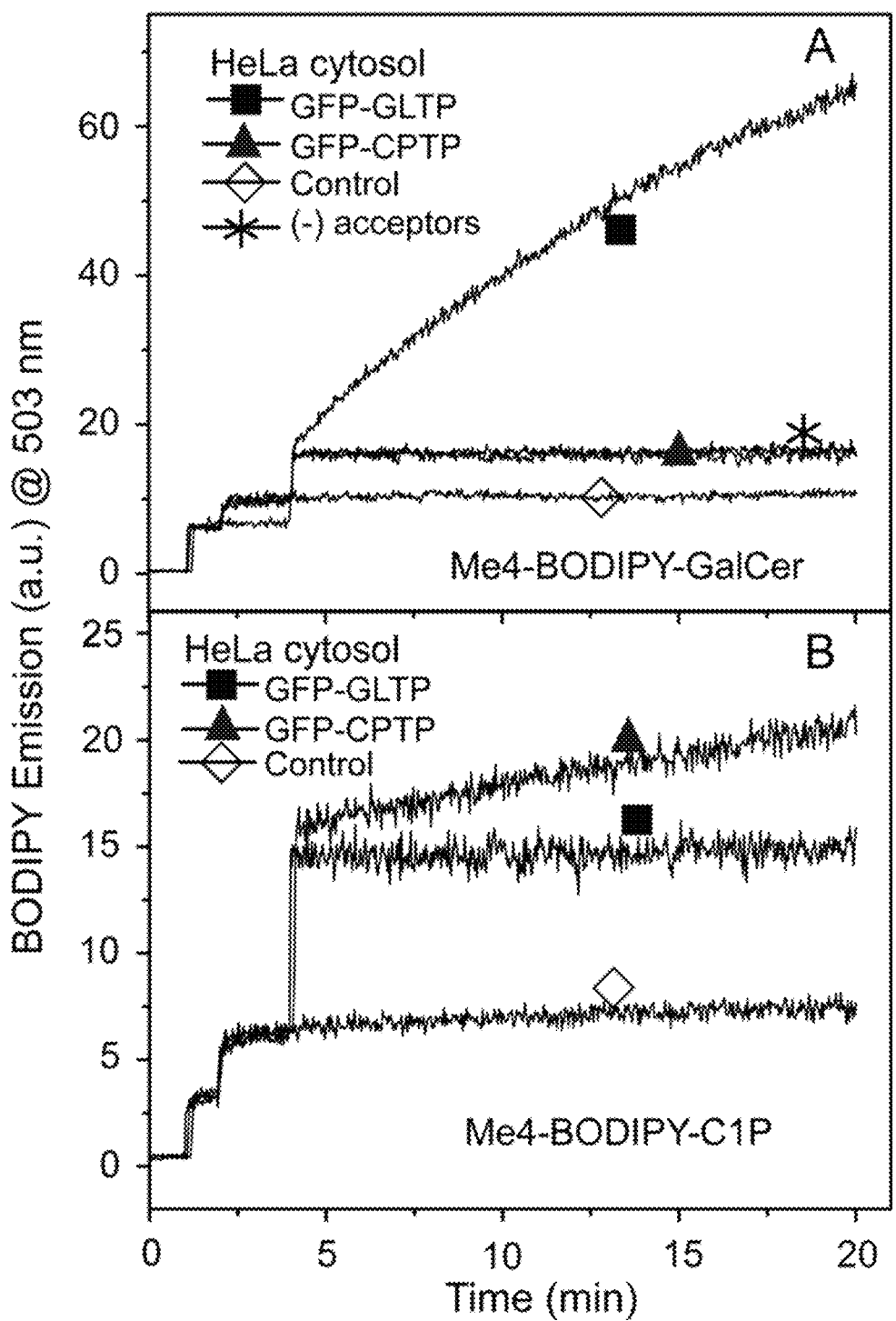
FIG. 14. Bicelle-dilution-model-membrane-assay detection of transfer activity by GLTP and CPTP expressed in HeLa cells after transient transfection with GFP-GLTP or GFP-CPTP. Cells were disrupted by brief probe sonication (30 sec×2) on ice. Cell supernatants were recovered by benchtop centrifugation (5 min @ 12,000 rpm) at 4° C. and then 10 µl aliquots were assayed for LTP activity. (Donor: q=0.5; Acceptor: q=0.5).

One can determine whether the b-d-model-membrane-to-b-d-model-membrane transfer assay conditions are suitable for reliable detection of sphingolipid transfer and specificity by different SLTPs within the cellular milieu. FIG. 14 shows the results obtained using lysates of HeLa cell overexpressing GFP-GLTP or GFP-CPTP. The sudden sharp increase in emission at 503 nm reflects addition of GFP protein (Em$_{max}$=509 nm). The ensuing slower but steadily increasing emission intensity reflects bd-vesicle-to-bd-vesicle transfer of Me$_4$-BODIPY GalCer by GFP-GLTP but not by GFP-CPTP (FIG. 14A). In contrast, Me$_4$-BODIPY C1P transfer by GFP-CPTP, but not by GFP-GLTP, is shown in FIG. 14B. Thus, the bd-vesicle-to-bd-vesicle transfer assay performs reliably in the presence of various other components present in crude cytosolic fractions.

Thus, this disclosure describes the use of POPC/DHPC bicelle-dilution model membrane vesicles providing an effective and efficient way to measure the intermembrane transfer of specific lipids by various lipid transfer proteins while avoiding the challenges associated with liposomal bilayer vesicles. In contrast, conventional in vitro measurement of lipid intermembrane transfer has typically relied on biomembrane mimetics such as liposomal bilayer vesicles. This reliance has limited the development of easy and straightforward lipid transfer assays because of the inherent challenges associated with bilayer vesicles including, for example, time-consuming preparation methodologies and short shelf-life that necessitate fresh vesicle preparation to carry out high-quality lipid transfer assays.

One aspect of the lipid transfer assay described herein is the ease and simplicity of preparing of donor and acceptor model membrane preparation by dilution of 0.5 q-value POPC/DHPC mixtures. Preparation involves simple lipid mixing, solvent removal, hydration, and mild agitation at room temperature. The ensuing re-equilibration of DHPC into the surrounding aqueous milieu results in spontaneous formation of small unilamellar vesicles that serve as the donor and acceptor model membranes. Simple dilution of 0.5 q-value POPC/DHPC mixtures at room temperature, along with mild agitation, results in formation of unilamellar vesicles with a narrow size distribution (32 nm to 36 nm diameter) that are stable and ideal for measuring LTP-mediated lipid transfer. Moreover, use of bicelle-dilution unilamellar vesicles in conjunction with the highly sensitive FRET approach described herein uses well less than 1% of the resources (e.g., lipids, lipid fluorophores) compared to assays using conventional bicelles.

Certain topological aspects of the physiological situation are accommodated by the assay design. In mammals, simple sphingolipids such as glucosylceramide and ceramide-1-phosphate are produced anabolicly by glucosylceramide synthase and ceramide kinase, respectively, at specific locations on the cytosolic face of the Golgi, prior to transport by GLTP and CPTP to other intracellular sites. To model this physiological situation, the sphingolipids are initially confined to the sphingolipid source (donor) bicelle-generated model membranes and not present in the receiver (acceptor) bicelle-generated model membranes prior to transfer by protein.

The use of bicelle-dilution vesicles provides similar sensitivity and reproducibility as other small vesicle assays but without the need for preparing fresh model membranes prior to assaying. In fact, bicelle-generated model membrane stocks can be repeatedly frozen and thawed without diminishing assay performance. One features of the lipid transfer assay described herein is easy and fast production of bicelle-generated vesicles by simple dilution that avoids lipid fluorophore degradation. A second feature of the lipid transfer assay described herein is stability and relatively long shelf-life after production, including freezer storage without detrimental effects to FRET assay performance.

Thus, the use of bicelle-dilution generated unilamellar vesicles in conjunction with FRET-based lipid monitoring provides a straightforward and easy lipid transfer assay with improved sensitivity, stability, and/or reproducibility compared to other conventional vesicle systems. The bd-vesicle-to-bd-vesicle assay is sufficiently robust for real-time detection of sphingolipid transfer activity and sphingolipid specificity by various LTPs, not only when purified, but also when present in crude cytosolic fractions recovered from cell homogenates.

The lipid transfer assay described herein can be adapted to provide a platform for the development of designer LTP assay kits for monitoring the activity of various LTPs with known lipid specificity and/or identifying the lipid specificity of newly discovered proteins that potentially function as LTPs. Moreover, adapting the assay to high-throughput formats can provide a highly sensitive and robust method for the screening of large libraries of small-molecule compounds to identify inhibitors of various lipid transfer proteins. Identified inhibitors can enable development of new drugs for treatments of inflammation, cardiovascular diseases, and other pathologies associated with abnormal lipid transfer protein expression and activities.

C2-Domain Binding

The bicelle-dilution method can be used to generate model membranes for other applications. For example, the bicelle-dilution model membranes can be used to evaluate binding interactions between membranes and membrane-binding proteins such as, for example, proteins that include a C2 domain. A C2 domain is a protein structural domain involved in targeting proteins to cell membranes. A C2 domain is often coupled to an enzymatic domain and therefore functions to bring the enzymatic domain of the protein into proximity with a membrane.

Cytoplasmic phospholipase A2 is an exemplary protein that includes a C2 domain. Cytoplasmic phospholipase A2 is not an lipid transfer protein, but is a high-affinity membrane binding domain that enables various proteins to interact with membranes. Fluorescence resonance energy transfer techniques can be used to monitor C2-domain-protein binding to model membranes.

While illustrated in the context of an exemplary embodiment in which the protein having a C2 domain is cytoplasmic phospholipase A2, b-d model membranes can be used to evaluate binding between membranes and any protein that interacts directly with membranes, including other proteins that include C2 domains. Exemplary additional proteins whose functionality involves interacting with a biological membrane—e.g., involve translocation from the cytoplasm to the membranes—include, but are not limited to, signaling kinases, lipases, etc.

Figure 18:
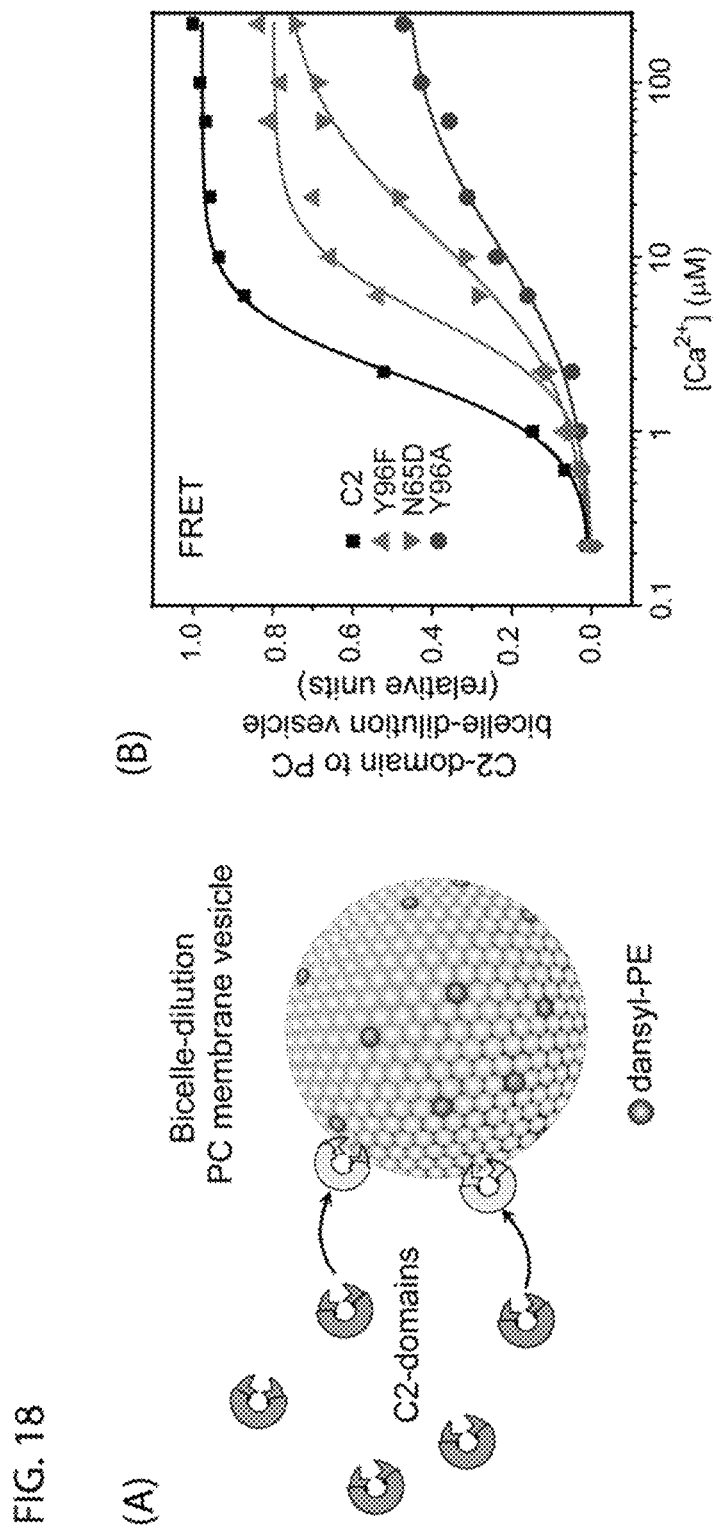
FIG. 18. Use of bicelle-dilution vesicles for assessing protein binding to membranes. (A) C2-domain binding to POPC bilayers formed by POPC-DHPC bicelle dilution and containing 5 mole % dansyl-phosphatidylethanolamine (PE). Förster resonance energy transfer involving Trp/Tyr excitation in C2-domain results in increased dansyl-PE emission (and decreased Trp/Tyr emission) when the C2-domain binds to the bicelle-dilution PC membrane vesicles. (B) FRET binding isotherms showing the $Ca^{2+}$ dependence of point mutant and control protein (0.5 mM) equilibrium adsorption to POPC-DHPC bicelle-dilution vesicles (4 mM).

FIG. 18 and FIG. 19 show data using b-d model membranes to assess protein binding to membranes. FIG. 18A illustrates interaction between a protein with a C2 domain and a b-d model membrane. FIG. 18B shows data demonstrating the $Ca^{2+}$ dependence of point mutant and control protein equilibrium adsorption to POPC-DHPC bicelle-dilution vesicles. The C2 domain point mutants tested in FIG. 18 and FIG. 19 involve an interaction site in the C2 domain that is specific for the polar head group of phosphatidylcholine.

FIG. 19A provides FRET data showing the POPC-DHPC bicelle-dilution vesicle dependence of point mutant and control protein equilibrium adsorption at 50 mM $Ca^{2+}$, while FIG. 19B shows the relative binding affinity of C2 domain point mutants and control (WT) cytoplasmic phospholipase A2.

The data in FIG. 18 and FIG. 19 demonstrate that, in addition to bicelle-dilution model membranes being useful for monitoring lipid transfer between membranes, can measure protein binding to lipid vesicles.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

Examples

Materials

1-Palmitoyl-2-oleyl-sn-glycero-3-phosphocholine (POPC) and 1,2-hexanoyl-sn-glycero-3-phosphocholine (DHPC) were purchased from Avanti Polar Lipids (Alabaster, Ala.) and used without further purification. Sphingolipids (SLs) labeled with N-[15-(4,4-difluoro-1,3,5,7-tetramethyl-4-bora-3a,4a-diaza-s-indacene-8-yl)] pentadecanoyl acyl chains (e.g. $Me_4$-BODIPY-15-ceramide-1-phosphate (C1P) or $Me_4$-BODIPY-15-galactosylceramide (GalCer)) were synthesized by reacylation of sphingosine-1-phosphocholine followed by phospholipase D treatment as previously described (Boldyrev et al., 2013, Russ. *J. Bioorgan. Chem.* 39: 539-542) or by reacylation of galactosyl(β)-sphingosine as previously described (Boldyrev et al., 2007, *J Lipid Res.* 48:1518-1532), and then purified.

Preparation of Bicelle-Dilution Model Membrane Vesicles

Bicelle-dilution model membranes at q-values ranging from 0.1 to 2 were prepared by combining the appropriate amounts of POPC, BODIPY-15-SL (1 mole %), DiI-C18 (1.5 mole %) and DHPC from stock solutions in hexane/ethanol or chloroform and then drying under nitrogen to remove all traces of solvent. Resuspension in assay buffer and vigorous vortexing enabled production of stocks with q-values of 0.1 or 0.5 to achieve optical clarity and homogeneity. The stocks with q-values of 1 or 2 were vortexed and sonicated until they were clear and homogeneous. All b-d model membrane samples [q=(POPC+BODIPY-15-SL+DiI-C18)/DHPC or POPC/DHPC] were centrifuged for 10 minutes at 13,000 rpm in a benchtop microcentrifuge (Spectrofuge Corporation of NC, Inc., Durham, N.C.; 1.5 ml tubes) before using.

Stock Donor and Acceptor Preparation and Use in Lipid Transfer Assay

For experiments requiring ~10 kinetic assays, donor stock lipid mixtures (0.5 q-value) were prepared by combining POPC (0.39 μmol), BODIPY-15-SL (0.004 μmol), DiI-C18 (0.006 μmol) and DHPC (0.8 μmol) from stock solvent solutions of hexane/ethanol (9:1) or chloroform/methanol (8:2). Acceptor stock lipid mixtures (0.5 q-value) were prepared by combining POPC (2 μmol) and DHPC (4 μmol) from stock solvent solutions. Total solvent volume in the clean glass vials containing inverted conical bottoms was approximately 100 μl. For other q-value stocks, the amount of DHPC was adjusted accordingly. Dry films of the lipid mixtures were obtained using a stream of nitrogen to evaporate all solvent at room temperature. The dry lipid films were hydrated by adding 200 μl of assay buffer (10 mM potassium phosphate, pH 6.6, 150 mM NaCl, and 0.2% EDTA) and then vortexed vigorously for at least five minutes to achieve optical clarity. For stocks with q-values of 1 or 2, lipid mixtures were not only vortexed vigorously but also sonicated briefly (2 to 3 minutes). All stocks were equilibrated overnight at room temperature prior to use in the lipid transfer assay regardless of q-value [q-value for donors=(POPC+BODIPY-15-SL+DiIC18)/DHPC; q-value for acceptors=POPC/DHPC]. Immediately prior to use in the FRET lipid transfer assay, donor and acceptor stocks were centrifuged for 10 minutes at 13,000 rpm. The FRET lipid transfer assay as performed as follows: donor stock (20 μl) was diluted into a stirred temperature-controlled cuvette containing assay buffer an equilibrated for two minutes to ensure a stable signal response. Next, acceptor stock (20 μl was diluted into the stirred cuvette and equilibrated for four minutes prior to initiating sphingolipid transfer by adding lipid transfer protein (2 μg) to a final cuvette volume of 2.5 ml. The total lipid concentration was 288 μM for assays using a 5:1 acceptor-to-donor ratio and was higher when more acceptors were added to increase transfer equilibrium from the donors.

Fluorescent Lipid Transfer Between Membranes

Real-time intermembrane transfer rates of fluorescent sphingolipids were obtained by Förster resonance energy transfer (FRET) using a SPEX FluoroLog3 spectrofluorometer (Horiba Scientific, Ltd., Kyoto, Japan), with excitation and emission band passes of 2 nm and a stirred (~100 rpm), temperature-controlled (25±0.1° C.) sample cuvette holder. All fluorescent lipids were localized initially to the SL-source (donor) vesicles (formed by rapid ethanol injection or probe sonication) or SL-source (donor) b-d model membranes. Minimal BODIPY-lipid emission occurred upon excitation (460 nm) due to resonance energy transfer to nearby C18-DiI. Either sonicated POPC vesicles or b-d POPC/DHPC model membranes served as receiver (acceptor) model membranes, which produced minimal change in fluorescence signal when added in excess (Mattjus et al., 1999, *Anal. Biochem.* 268:297-304). The final receiver (acceptor) vesicle concentration in the FRET lipid transfer assay was ~240 µM to 1440 µM, which was five-fold to 30-fold higher than the SL-source (donor) vesicle concentration. Protein addition triggered a sudden, hyperbolic increase in BODIPY emission intensity (503 nm) as FRET decreased due to protein transport of fluorescent glycolipids from SL-source (donor) vesicles to receiver (acceptor) vesicles, creating separation from nontransferable $C_{18}$-DiI lipid, as the protein delivers the BODIPY-SL to the excess POPC receiver vesicles or POPC/DHPC bicelles. Addition of Tween-20 detergent after extended incubation provided a measure of maximum intensity achievable by "infinite" fluorophore separation.

Light-Scattering Measurements

Light scattering was measured at 90° relative to incident light using a SPEX FluoroLog3 spectrofluorometer (Horiba Scientific, Ltd., Kyoto, Japan). The intensity detected by the emission monochrometer while irradiating at 320 nm was measured as a function of time to assess changes in bicelle aggregation or fusion state when using the FRET lipid transfer assay conditions as previously described (Mattjus et al., 1999, *Anal. Biochem.* 268:297-304).

Dynamic light scattering (DLS) readings were measured with a Zetasizer Nano ZS (Malvern, Worcestershire, UK) using noninvasive backscatter optics. Lipid mixtures were buffered at pH 6.6 in 10 mM potassium phosphate, 150 mM NaCl, and 0.2% EDTA. Samples were equilibrated at room temperature for 10 minutes before measurement. All measurements used 1-cm path length quartz cuvettes. Mean $R_h$ was calculated from the diffusion coefficient D, solvent viscosity η, and the Stokes-Einstein relationship $R_h=kT/6\pi\eta D$, where k is the Boltzmann constant and T is temperature in Kelvin.

Recombinant Protein Purification

Cloning, expression, and purification of GLTP, ACD11, and CPTP have been described previously (Lin et al., 2000, *J. Biol. Chem.* 275:5104-5110; Li et al., 2004, *Biochemistry* 43:10285-10294; Malakhova et al., 2005, 1 *Biol. Chem.* 280:26312-26320; Simanshu et al., 2013, *Nature* 500:463-467; Simanshu et al., 2014, *Cell Rep.* 6:388-399). Human GLTP ORF (GenBank AF209704), *Arabidopsis* acd11 (NCBI NP_181016.1) and human CPTP (GenBank JN542538 and NP_077792.2) open reading frames were ligated into modified pET-28-SUMO vectors (kanamycin-resistance; Invitrogen, Thermo Fisher Scientific, Inc., Carlsbad, Calif.) using the BamHI and SalI restriction sites. Transformation of BL21 (DE3)-pLysS or -Star cells enabled expression of proteins N-terminally-tagged with 6×His-SUMO. Transformed cells were grown in Luria-Bertani medium at 37° C. for six hours, induced with 1 mM IPTG, and then incubated 16-20 hours at 20° C. Affinity protein purification from soluble lysate was accomplished by Ni-NTA affinity chromatography. Cleavage of N-terminal 6×His-SUMO tag was carried out with SUMO protease, Ulp1, overnight at 4° C. Affinity repurification by Ni-NTA chromatography followed by FPLC gel filtration chromatography (HiLoad 16/60 Superdex-75 prep grade column; GE Healthcare, Chicago, Ill.), equilibrated in 25 mM Tris-HCl (pH 8.0) containing 100 mM NaCl and 1 mM DTT, yielded proteins with native sequences. Pooled peak fractions were concentrated by centrifugal concentrators (VIVASPIN, Sartorius AG, Gottingen, Germany; 10 kDa cutoff). Protein purity was confirmed by SDS-PAGE (Li et al., 2004) before freezing the pure proteins in buffer containing 50% glycerol and storing at −20° C.

HeLa Cell Lysate Preparation

HeLa cells were plated on 100-mm dishes and transfected with different vectors using Lipofectamine 2000 (Invitrogen, Carlsbad, Calif.). At 24 hours post-transfection, cells were harvested by trypsinization, washed with phosphate-buffered saline (PBS) by benchtop centrifugation and then suspended in PBS buffer (200 µl). Disruption of the HeLa cells was accomplished by brief probe sonication (2×30 seconds) on ice. Cell supernatants were recovered by benchtop centrifugation (5 minutes at 12,000 rpm) at 4° C. and 10 µl aliquots were assayed for SLTP activity using donor bicelle-dilution vesicles containing either Me4-BODIPY-GalCer or Me4-BODIPY-C1P along with C18-DiI.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An assay system for measuring transfer of lipid from a donor model biomembrane to an acceptor model biomembrane, the system comprising:
   a donor model biomembrane comprising a lipid, the lipid comprising a detectable label;
   a lipid transfer protein that specifically binds the lipid comprising the detectable label; and
   an acceptor model biomembrane;
   wherein at least one of the donor model biomembrane and the acceptor model biomembrane is a bicelle-dilution model membrane, the bicelle-dilution model membrane comprising:
      a first layer of long-chain phosphoglycerides comprising:
         polar head groups forming a first outer surface; and
         nonpolar tails; and
      a second layer of long-chain phosphoglycerides comprising:
         polar head groups forming a second outer surface; and
         nonpolar tails;
   the nonpolar tails of the first layer of long-chain phosphoglycerides and the nonpolar tails of the second layer of long-chain phosphoglycerides arranged end-to-end forming a hydrophobic core.

2. The assay system of claim 1, wherein both the donor model biomembrane and the acceptor model biomembrane are bicelle-dilution model membranes.

3. The assay system of claim 1, wherein:
   the donor model biomembrane is a bicelle-dilution model membrane; and
   the acceptor model biomembrane comprises a conventional vesicle, a conventional micelle, or a conventional nanodisc.

4. The assay system of claim 1, wherein:
   the donor model biomembrane comprises a conventional vesicle, a conventional micelle, or a conventional nanodisc; and
   the acceptor model biomembrane is a bicelle-dilution model membrane.

5. The assay system of claim 1, wherein the bicelle-dilution model membrane consists of:
   a first layer of long-chain phosphoglycerides comprising:
      polar head groups forming a first outer surface; and
      nonpolar tails; and
   a second layer of long-chain phosphoglycerides comprising:
      polar head groups forming a second outer surface; and
      nonpolar tails;
   the nonpolar tails of the first layer of long-chain phosphoglycerides and the nonpolar tails of the second layer of long-chain phosphoglycerides arranged end-to-end forming a hydrophobic core.

6. The assay system of claim 5, wherein the long-chain phosphoglyceride comprises a hydrocarbon chain comprising at least nine carbons.

7. The assay system of claim 6, wherein the long-chain phosphoglyceride comprises 1-palmitoyl-2-oleoyl phosphatidylcholine (POPC).

8. The assay system of claim 1, wherein the detectable label comprises a fluorescent marker.

9. The assay system of claim 1, wherein the long-chain phosphoglyceride comprises a hydrocarbon chain comprising at least nine carbons.

10. The assay system of claim 9, wherein the long-chain phosphoglyceride comprises 1-palmitoyl-2-oleoyl phosphatidylcholine (POPC).

* * * * *